US005643723A

United States Patent [19]

Persing et al.

[11] Patent Number: 5,643,723

[45] Date of Patent: Jul. 1, 1997

[54] DETECTION OF A GENETIC LOCUS ENCODING RESISTANCE TO RIFAMPIN IN MYCOBACTERIAL CULTURES AND IN CLINICAL SPECIMENS

[75] Inventors: David H. Persing; John J. Hunt, both of Rochester, Minn.; Karen K. Y. Young, San Ramon, Calif.; Teresa A. Felmlee, Oronoco, Minn.; Glenn D. Roberts; A. Christian Whelan, both of Rochester, Minn.

[73] Assignees: Roche Molecular Systems, Inc., Branchburg, N.J.; Mayo Foundation For Medical Education and Research, Rochester, Minn.

[21] Appl. No.: 250,030

[22] Filed: May 26, 1994

[51] Int. Cl.$^6$ .............................. C12Q 1/68; C12P 19/34; C07H 21/04; C12N 15/00

[52] U.S. Cl. ............................ 435/6; 435/91.1; 435/91.2; 435/863; 536/24.33; 536/23.7; 536/24.32; 935/8; 935/76; 935/77; 935/78

[58] Field of Search .................................. 435/5, 6, 91.1, 435/91.2, 183, 863; 536/24.33, 23.7, 24.32; 935/76–78, 8

[56] References Cited

U.S. PATENT DOCUMENTS

| | | | |
|---|---|---|---|
| 4,458,066 | 7/1984 | Caruthers . | |
| 4,683,194 | 7/1987 | Saiki et al. . | |
| 4,683,195 | 7/1987 | Mullis et al. . | |
| 4,683,202 | 7/1987 | Mullis . | |
| 4,800,159 | 1/1989 | Mullis et al. | 435/172.3 |
| 5,023,171 | 6/1991 | Ho et al. . | |

FOREIGN PATENT DOCUMENTS

| | | | |
|---|---|---|---|
| 03957 | 2/1988 | WIPO | C12Q 1/68 |
| 9322454 | 11/1993 | WIPO . | |

OTHER PUBLICATIONS

S.L. Beaucage et al., "Deoxynucleoside Phosphoramidites—A New Class of Key Intermediates in Deoxypolynucleotide Synthesis," *Tetrahedron Lett.*, 22, 1859–1862 (1981).

R. Boom et al., "Rapid and Simple Method for Purification of Nucleic Acids," *J. Clin. Microbiol.*, 28, 495–503 (1990).

E.L. Brown et al., "Chemical Synthesis and Cloning of a Tyrosine tRNA Gene," *Meth. Enzymol.*, 68, 109–151 (1979).

K.D. Eisenach et al., "PCR Detection of *Mycobacterium tuberculosis*," in *Diagnostic Molecular Microbiology: Principles and Applications*, D.H. Persing et al., Eds., Washington, American Society for Microbiology, 191–196 (1993).

J.N. Engel et al., "Cloning and Characterization of RNA Polymerase Core Subunits of *Chlamydia trachomatis* by Using the Polymerase Chain Reaction," *J. Bacteriology*, 172, 5732–5741 (1990).

M. Finken et al., "Molecular Basis of Streptomycin Resistance in *Mycobacterium tuberculosis*: Alterations of the Ribosomal Protein S12 Gene and Point Mutations Within a Functional 16S Ribosomal RNA Pseudoknot," *Molecular Microbiol.*, 9, 1239–1246, (1993).

M.A. Fischl et al., "An Outbreak of Tuberculosis Caused by Multiple–Drug–Resistant Tubercle Bacilli Among Patients with HIV Infection," *Ann. Intern. Med.*, 117, 177–183 (1992).

T.R. Frieden et al., "The Emergence of Drug–Resistant Tuberculosis in New York City," *N. Engl. J. Med.*, 328, 521–526 (1993).

M. Goble et al., "Treatment of 171 Patients with Pulmonary Tuberculosis Resistant to Isoniazid and Rifampin," *N. Engl. J. Med.*, 328, 527–532 (1993).

J. Goodchild, "Conjugates of Oligonucleotides and Modified Oligonucleotides: A Review of Their Synthesis and Properties," *Bioconjugate Chem.*, 1, 165–187 (1990).

J.J. Goswitz et al., "Detection of gyr A Gene Mutations Associated with Ciprofloxacin Resistance in Methicillin–Resistant *Staphylococcus aureus*: Analysis by Polymerase Chain Reaction and Automated Direct DNA Sequencing," *Antimicrob. Agents Chemother.*, 36, 1166–1169 (1992).

N. Honor, et al., "Molecular Basis of Rifampin Resistance in *Mycobacterium leprae*," *Antimicrob. Agents Chemother.*, 37, 414–418 (1993).

R.E. Huebner et al., "Current Practices of Mycobacteriology: Results of a Survey of State Public Health Laboratories," *J. Clin. Microbiol.*, 31, 771–775 (1993).

J. M. Hunt, et al., "Detection of a Genetic Locus Encoding Resistance to Rifampin in Mycobacterial Cultures and in Clinical Specimens," abstract (No. C–125) of poster presented at the 93rd General Meeting of the American Society for Microbiology, Atlanta, Georgia, Apr. 9, 1993.

P. Imboden et al., "Detection of Rifampin Resistance Mutations in *Mycobacterium tuberculosis* and *M. leprae*," in *Diagnostic Molecular Microbiology*, D. Persing et al., Eds., American Society for Microbiology, Washington; pp. 519–526 (1993).

D.J. Jin et al., "Mapping and Sequencing of Mutations on the *Escherichia coli* rpoB Gene That Lead to Rifampicin Resistance," *J. Mol. Biol.*, 202, 45–58 (1988).

(List continued on next page.)

*Primary Examiner*—Bradley L. Sisson
*Attorney, Agent, or Firm*—Schwegman, Lundberg, Woessner & Kluth, P.A.

[57] ABSTRACT

A method is provided for detecting M. tuberculosis or mutants thereof, particularly rifampin-resistant MTB, in a biological sample comprising: isolating DNA from the biological sample; amplifying the isolated DNA under hybridizing conditions with a primer set that targets portions of the gene encoding rpoB; wherein the pimer set comprises at least one primer that hybridizes under hybridizing conditions to at least one signature nucleotide for M. tuberculosis; and isolating and sequencing the amplified DNA to determine the presence or absence of M. tuberculosis or mutants thereof.

23 Claims, 14 Drawing Sheets

OTHER PUBLICATIONS

M.E. Levin et al., "*Mycobacterium smegmatis* RNA Polymerase: DNA Supercoiling, Action of Rifampicin and Mechanism of Rifampicin Resistance," *Molec. Microbiol.*, 8, 277–285 (1993).

S. Malawista, Principal Investigator, "Probes for *Borrelia burgdorferi* DNA in Ticks, Mice and Men," National Institutes of Health Grant No. AR30548 (FY 1994).

L.P. Miller et al., "*Mycobacterium tuberculosis* RNA Polymerase Beta–Subunit (rpoB) Gene, Complete Cds," GenBank Accession No. L27989, (Apr. 1, 1994).

S.A. Narange et al., "Improved Phosphotriester Method for Synthesis of Gene Fragments," *Meth. Enzymol.*, 68, 90–99 (1979).

R. Patel et al., "Isolation and Restriction Endonuclease Analysis of Mycobacterial DNA," *J. Gen. Microbiol.*, , 132, 541–551 (1986).

D.H. Persing, Principal Investigator, "Molecular Diagnosis and Monitoring of Lyme Disease," National Institutes of Health Grant No. AR41497 (FY 1994).

D.H. Persing, Principal Investigator, "Multi–Locus Molecular Detection of *Borrelia burgdorferi*," National Institutes of Health Grant No. AI32403 (FY 1994).

D.H. Persing et al., "In Vitro Nucleic Acid Amplification Techniques," in *Diagnostic Molecular Microbiology: Principles and Applications,* D.H. Persing et al., Eds., Washington, American Society for Microbiology, 51–87 (1993).

D.H. Persing et al., "Target Selection and Optimization of Amplification Reactions," in *Diagnostic Molecular Microbiology: Principles and Applications,* D.H. Persing et al., Eds., Washington, American Society for Microbiology, 88–104 (1993).

P.R. Quinn et al., *Mycobacteriology Laboratory Procedure Manual,* Division of Clinical Microbiology, Mayo Clinic, Rochester, MN (1992).

G.D. Roberts et al., Mycobacterium in *Manual of Clinical Microbiology, 5th Ed.;* A. Balows et al., Eds.; American Society for Microbiology: Washington; pp. 304–339 (1991).

J. Sambrook et al., *Molecular Cloning: A Laboratory Manual,* 2nd. Ed., Cold Spring Harbor Laboratory Press, Cold Spring Harbor, NY (1989). Enclosed is the Title page, Copyright page and Contents pages (pp. v–xxxii).

I.R. Sinkeldam et al., *Mycology Laboratory Procedure Manual,* Division of Clinical Microbiology, Mayo Clinic, Rochester, MN (1992).

P.M. Small et al., "Exogenous Reinfection with Multidrug–Resistant *Mycobacterium tuberculosis* in Patients with Advanced HIV Infection," *New Eng. J. Med.,* 328, 1137–1144 (1993).

A. Telenti et al., "Direct, Automated Detection of Rifampin–Resistant *Mycobacterium tuberculosis* by Polymerase Chain Reaction and Single–Strand Conformation Polymorphism Analysis," *Antimicrobial Agents and Chemotherapy,* 37, 2054–2058 (1993).

A. Telenti et al., "Detection of Rifampicin–Resistance Mutations in *Mycobacterium tuberculosis,*" *Lancet,* 341, 647–650 (1993).

A. Telenti et al., "*Mycobacterium tuberculosis* RNA Polymerase Beta Subunit; Rifampicin Resistance Gene, Complete Cds," GenBank Accession No. L05910 (May 21, 1993).

F.C. Tenover et al., "The Resurgence of Tuberculosis: Is Your Laboratory Ready?" *J. Clin. Microbiol.,* 31, 767–770 (1993).

F.C. Tenover et al., "Nucleic Acid Probes for Detection and Identification of Infectious Agents," in *Diagnostic Molecular Microbiology: Principles and Applications,* D.H. Persing et al., Eds., Washington, American Society for Microbiology, 3–25 (1993).

M. Tsukamura, "The Pattern of Resistance Development to Rifampicin in *Mycobacterium tuberculosis,*" *Tubercle,* 53, 111–117 (1972).

T.J. White, "Amplification Product Detection Methods," in *Diagnostic Molecular Microbiology: Principles and Applications,* D.H. Persing et al., Eds., Washington, American Society for Microbiology, 138–148 (1993).

F.G. Winder, "Mode of Action of the Antimycobacterial Agents and Associated Aspects of the Molecular Biology of Mycobacteria," in *The Biology of the Mycobacteria, vol. 1,* Ratledge et al., eds., Academic Press: New York, pp. 353–438 (1982).

T. Yamada et al., "Alteration of Ribosomes and RNA Polymerase in Drug–Resistant Clinical Isolates in *Mycobacterium tuberculosis,*" *Antimicrob. Agents Chemother.,* 27, 921–924 (1985).

Y. Zhang et al., "The Catalase–Peroxidase Gene and Isoniazid Resistance of *Mycobacterium tuberculosis,*" *Nature,* 358, 591–593 (1992).

Sommer and Tautz, "Minimal homology requirements for PCR primers", *Nucleic Acids Research,* vol. 17, No. 16, issued 1989, p. 6749.

Sigma Molecular Biology (Catalog), p. 54 1989.

Laszlo et al., *Bull World Health Org.,* (1994) 72(4) 603–10 abstract only.

A PARTIAL AMINO ACID SEQUENCE ALIGNMENT OF THE *rpo*B GENE

```
                  400                                                450
       M. leprae   l    k           s q         k  k    ar    y v kk
 M. tuberculosis   l    k           s q         k  k    ar    y v kk
         E. coli                   r     s                a         s l..
  S. typhimurium                   r     s                a
       P. putida                            n     a      pl         ri ..
       Consensus  LVEIYRMMRP GEPPTKEAAE TLFENLFFSE DRYDLS-VGR MKFNR-LGLH

                  451                                                500
       M. leprae  ag lit st  te    atie y  rlhe qs               t
 M. tuberculosis  vg pit st  te    atie y  rlhe qt               t
         E. coli   e                    k          .......... ..
  S. typhimurium   d                    k          .......... ..
       P. putida   t                    t          .......... ..i
       Consensus  R-EIEGSGIL SKEDIVDVMK -LVDIRNGKG TMTVPGGVEV PVEVDDIDHL

                  501                                                550
       M. leprae      l t     iq  i     s m  v r    ttq v ait   t   ir
 M. tuberculosis      l t     iq  i     s m  v r    ttq v ait   t   ir
         E. coli        s                             g l t
  S. typhimurium        s                             g l t
       P. putida        c                             a s g
       Consensus  GNRRIR-VGE MAENQFRVGL VRVERAVKER LSL-D-E-LM PQDLINAKPV
```

FIG. 1A

```
                 551                                                600
      M. leprae  v        t                gl      l         s
M. tuberculosis  v        t                gl      l         s
        E. coli  s                 v               i
 S. typhimurium  s                                 i            l
      P. putida  a                                 c
      Consensus  -AAVKEFFGS SQLSQFMDQN NPLSEITHKR R-SALGPGGL TRERAGFEVR

                 601                                                650
      M. leprae      s    m                g        v p   i
M. tuberculosis      s    m                g        v p   i
        E. coli                                   q  e            t
 S. typhimurium                                   q  e          r
      P. putida                               aa      q      s   v k
      Consensus  DVHPTHYGRV CPIETPEGPN IGLINSLSVY ARTN-YGFLE TPYRKVVDGV

                 651                                                700
      M. leprae       e  t  d  dr         pi  a r sssracw  r     veyvas
M. tuberculosis       v  t  d  dr         pi a  r    pr l  r     veyvps
        E. coli   t   h        gny        n     h        c s  .  sslfsr
 S. typhimurium   t   h        gny        n     h        c s  .  sslfsr
      P. putida       v        ad      saa n kkq       a  h l.n ftvkap
      Consensus  VSDEI-YLSA IEE--HVIAQ ANS-LD-EG- FVEDLVTVR- KAGE------
```

FIG. 1B

```
                   701                                                750
      M. leprae    s          r m    ta                              lv s r
M. tuberculosis    s          r m    ta                              lv s a
        E. coli     q        tq    g
 S. typhimurium     q        tq    g
      P. putida       tl      k                          s
      Consensus    DEVDYMDVSP -QVVSVAASL IPFLEHDDAN RALMGANMQR QAVPTLRADK
```

FIG. 1C

```
                                          * *
                                2
              M. nonchromo                t
              M. fortuitum      n
              M. fortuitum      n
              M. fortuitum      n
               M. chelonae     nn        t
               M. chelonae      ... ... ... ... ... ...
                 M. xenopi       n          t
               M. kansasii      ... ... ... ... ... ...
            M. avium-inter                n
            M. avium-inter       gc ag
            M. avium-inter       gc ag
            M. avium-inter      ngc ag
            M. avium-inter      ggc ag
            M. avium-inter        a
                  M. bovis      n         g t
           M. tuberculosis       n        g t n n    n
           M. tuberculosis                g t
           M. tuberculosis                g t
           M. tuberculosis                g t
    Telente Genbank L05910                g t
                 Consensus      CCG CAG ACC CTG ATC AAC
            Aerobic actino                  t
                  A. bovis      .   a n   g   c
               A. viscosus      .   a c       c
          N. brasilensis         n
          N. brasilensis
                 N. otitis        c n   n   g
               Rhodococcus       n      t g       g
               Rhodococcus      gtc tg  n   ac    t ncn
           Corynebacterium        c n c c        n   g
           Corynebacterium          ant t t t     t
           Corynebacterium       n        g   c
           Proprionibacter        n     n     c
           Proprionibacter      nn        n   c
```

*FIG. 2A*

```
         M. nonchromo        n                   c
         M. fortuitum        t   c   c   g   g
         M. fortuitum        t   c   c   g   g
         M. fortuitum        n   c   c   g   g
          M. chelonae      nt   c   c   g   g
          M. chelonae  ... ... ... ... ... ... ... ...
            M. xenopi        c   c       g
          M. kansasii  ... ... ... ... ... ... ... ...
       M. avium-inter                    g
       M. avium-inter                c
       M. avium-inter                c
       M. avium-inter        t   a   c   g   g
       M. avium-inter        c
       M. avium-inter        c       a           c
             M. bovis
     M. tuberculosis        n    n         n   nnn
     M. tuberculosis
     M. tuberculosis
     M. tuberculosis
     Telente Genbank  L05910
            Consensus  ATC CGG CCG GTG GTC GCC GCG ATC
       Aerobic actino        t   c   c   g  gg  t
             A. bovis            c     acg  n
          A. viscosus                  acg
      N. brasilensis    n   c          ng    n t
      N. brasilensis        c          ng    n t
            N. otitis        c   c   c   g n g  t
          Rhodococcus       n                g       g
          Rhodococcus   n   ct  tc  gc ccg  nn ng
     Corynebacterium  g g tc     c     t t   g   c
     Corynebacterium  g     t       c tct   t t     t
     Corynebacterium       nt    c   c      n
     Proprionibacter        c          acg  nt  n
     Proprionibacter       nc          acg   t
```

*FIG. 2B*

| | | | | | | | | |
|---|---|---|---|---|---|---|---|---|
| M. nonchromo | | | | | | | | |
| M. fortuitum | | | | | a | g | tcg | |
| M. fortuitum | | | | | a | g | tcg | |
| M. fortuitum | | | | | a | g | tcg | |
| M. chelonae | | | | | a | | | |
| M. chelonae | ... | ... | ... | ... | ... | ... | ... | ... |
| M. xenopi | | | | | | | | |
| M. kansasii | ... | ... | ... | ... | ... | ... | ... | ... |
| M. avium-inter | | | | | | | | |
| M. avium-inter | | | | | | | | |
| M. avium-inter | | | | | | | | |
| M. avium-inter | | | | | | | | |
| M. avium-inter | | | | | | | | |
| M. avium-inter | | | | | | | | |
| M. bovis | | | | | | | | |
| M. tuberculosis | | n | | | n | n | | |
| M. tuberculosis | | | | | | | | |
| M. tuberculosis | | n | | | | | | |
| M. tuberculosis | | | | | t | | | |
| Telente Genbank | L05910 | | | | | | | |
| Consensus | AAG | GAG | TTC | TTC | GGC | ACC | AGC | CAG |
| Aerobic actino | | | | | | | | |
| A. bovis | | n | | | | | tct | |
| A. viscosus | | | | | | | tc | |
| N. brasilensis | | | | | n | | tc | |
| N. brasilensis | | | | | a | | tc | |
| N. otitis | c | | n | c | cn | n | tcg | |
| Rhodococcus | | | | | | | tcg | |
| Rhodococcus | n | | nn | n | ag | ngg | cag | g |
| Corynebacterium | cnc | a | | n | n | c | tc | |
| Corynebacterium | cgc | a | | t | t | t | tc | |
| Corynebacterium | | | | | a | | tcg | |
| Proprionibacter | | n | | | n | | tc | |
| Proprionibacter | | | | | | | tc | |

*FIG. 2C*

```
                     **    *
                                                91
   M. nonchromo       g-
   M. fortuitum        g     n         t
   M. fortuitum        g     n         t
   M. fortuitum        g     n         t
    M. chelonae       g
    M. chelonae  ... ... ...
      M. xenopi    c   g               t
    M. kansasii  ... ... ...           n     n n
 M. avium-inter    c
 M. avium-inter        g
 M. avium-inter      ag
 M. avium-inter
 M. avium-inter        g
 M. avium-inter    c
       M. bovis      ag    a          n
M. tuberculosis  n   ag    a
M. tuberculosis      ag    a          n
M. tuberculosis  n   ag    a          n
M. tuberculosis      ag   ta
Telente Genbank      ag    a
      Consensus  CTG TCC CAG TTC ATG GAC CAG AAC
 Aerobic actino        g     cn
       A. bovis    c ag
    A. viscosus    c ag
N. brasilensis   t c   g             atg     g
N. brasilensis   t c   g             atg     g
      N. otitis  t c a n n     n   n   t     c g
    Rhodococcus        g                     cg
    Rhodococcus  g t c   a
Corynebacterium  n c     a   a    a   n      nnn
Corynebacterium                t
Corynebacterium        g               t
Proprionibacter    c   g
Proprionibacter    c   g
```

FIG. 2D

| | | | | | | | | | | | | | | | | | | |
|---|---|---|---|---|---|---|---|---|---|---|---|---|---|---|---|---|---|---|
| | | | | | | | | | | | | | | | * | * | | |
| | | 92 | | | | | | | | | | | | | | | | |
| M. nonchromo | | | | | | | | | | | | a | | | | | | |
| M. fortuitum | | | | | | | | | | | | | | | | | | |
| M. fortuitum | | | | | | | | | | | | | | | | | | |
| M. fortuitum | | | | | | | | | | | | | | | | | | |
| M. chelonae | | | | | | | | | | | | | | | c | | | |
| M. chelonae | | n | | | | | n | | t | g | | | | | | | | |
| M. xenopi | | | | | | | | | | | | | | | g | | | c |
| M. kansasii | | n | n | | | n | | | n | | | | | | c | | | c |
| M. avium-inter | | | | | | | | | | | | | | | | | | |
| M. avium-inter | | | | | | | | | | | | c | | | g | | | |
| M. avium-inter | | | | | | | | | | | | c | | | | | | |
| M. avium-inter | | | | | | | | | | | | | | | g | | | c |
| M. avium-inter | | | | | | | | | | | | | | | | | | |
| M. avium-inter | | | | | | | | | | | | | | | c | | | |
| M. bovis | | | | | | | | | | | | | | | g | t | | |
| M. tuberculosis | | | | | | | | | | | | | | | g | t | | |
| M. tuberculosis | | | | | | | | | | | | | | | g | t | | |
| M. tuberculosis | | | | | | | | | | | | | | | g | t | | |
| M. tuberculosis | | | | | | | | | | | | | | | g | t | | |
| Telente Genbank L05910 | | | | | | | | | | | | | | | g | t | | |
| Consensus | A | A | C | C | C | G | C | T | G | T | C | G | G | G | T | C | T | G |
| Aerobic actino | | | | | | | | | | | | | | | | | | |
| A. bovis | | | | | | | | | | g | | | | | | | | |
| A. viscosus | | | | | | | | | | g | | | | | c | | | |
| N. brasilensis | | | | | | | n | | c | g | | c | | | n | | | c |
| N. brasilensis | | | | | | | n | | c | g | | c | | | n | | | c |
| N. otitis | | g | n | | | | g | | | n | | | | | n | n | | |
| Rhodococcus | | | | | | | | | | g | | | a | | c | | | |
| Rhodococcus | | | | | | | | | | | | | | | | | | |
| Corynebacterium | | | n | n | | c | | | | | | t | | | c | | | |
| Corynebacterium | | | | t | | | | | | | | t | | | | | | |
| Corynebacterium | | | | | | | | | c | g | | | | | | | | |
| Proprionibacter | | | | | | | t | | | g | | c | | a | g | a | | |
| Proprionibacter | | | | | | | t | | | g | | c | | a | g | a | | |

FIG. 2E

| | | | | | | | | | | | | | | | | | | | | | | | | |
|---|---|---|---|---|---|---|---|---|---|---|---|---|---|---|---|---|---|---|---|---|---|---|---|---|
| | | | | | | | | | | | | | | * | | | | | | | | | | |
| M. nonchromo | | | | | | | | | | | g | | | t | | | | | | | | | | |
| M. fortuitum | | | | | | | | | | | t | | | t | | | | | | | | | | |
| M. fortuitum | | | | | | | | | | | t | | | t | | | | | | | | | | |
| M. fortuitum | | | | | | | | | | | t | | | t | | | | | | | | | | |
| M. chelonae | | | | | | | | | | | t | | | t | | | | | | | | | | |
| M. chelonae | | | | | | | | | | n | | t | n | | t | | | | | | | | | t |
| M. xenopi | | | | | | | | | | | | g | | | g | | | c | | | | | | |
| M. kansasii | | | | | | | | | | | | | | | g | | | t | | | | | | |
| M. avium-inter | | | | | | | | | | | | | | | | | | | | | | | | |
| M. avium-inter | | | | | | | | | | | | t | | | | | | | | | | | | |
| M. avium-inter | | | | | | | | | | | | | | | | | | c | | | | | | |
| M. avium-inter | | | | | | | | | | | | | | | | | | | | | | | | |
| M. avium-inter | | | | | | | | | | | | | | | | | | | | | | | | |
| M. avium-inter | | | | | | | | | | n | | | | | g | | | t | | | | | n | |
| M. bovis | | | | | | | | | | | | | | | a | | | | | | | | | |
| M. tuberculosis | | | | | | | | | | | | | | | a | | | | | | | | | |
| M. tuberculosis | | | | g | | | | | | | | | | | a | | | | | | | | | |
| M. tuberculosis | | | | | | | | | | | | | | | a | | | | | t | | | | |
| M. tuberculosis | | | | | | | | | | | | | | | a | | | | | | | | | |
| Telente Genbank L05910 | | | | | | | | | | | | | | | a | | | | | | | | | |
| Consensus | A | C | C | C | A | C | A | A | G | C | G | C | C | G | C | C | T | G | T | C | G | G | C | G |
| Aerobic actino | | | | | | | | | | | | t | | | | | | | | | | | | |
| A. bovis | | | | | | | | | | | | | | | | | | | a | g | c | | | c |
| A. viscosus | | | | | | | | | | | | | | | | | | | a | g | c | | | c |
| N. brasilensis | | | n | | | | | | | | | t | | | | | | n | | | c | | | c |
| N. brasilensis | | | n | | | | | | | | | t | | | | | | n | | | c | | | c |
| N. otitis | | | | a | | | | g | | n | | n | | | g | g | | c | n | n | | | t | |
| Rhodococcus | | | | a | | | | n | | | n | g | | | g | | n | | | | c | | | |
| Rhodococcus | | | g | | | | | | | | | t | | | | | | c | | | | | | t |
| Corynebacterium | | | | a | | | | | | | | t | | | t | | | | | | t | | | c |
| Corynebacterium | | | | | | | | | | | | t | | | t | | | c | | | c | | | |
| Corynebacterium | | | | | | | | | | | | | | | | | | c | | | | | | |
| Proprionibacter | | | g | | | | c | g | t | | | t | | | t | | | | | | | | | c |
| Proprionibacter | | | g | | | | c | g | c | | | t | | | | | | | | | | | | c |

```
                       *                   *

   M. nonchromo               t           g
   M. fortuitum
   M. fortuitum
   M. fortuitum
    M. chelonae               t         a
    M. chelonae               t cng   t a     g
      M. xenopi    t   t   g               g   c
    M. kansasii        g   g                   g
 M. avium-inter            g
 M. avium-inter
 M. avium-inter
 M. avium-inter            g   t               g
 M. avium-inter               t
 M. avium-inter                     t
       M. bovis        g                   a
M. tuberculosis        g                   a
M. tuberculosis        g                   a
M. tuberculosis        g           n       a
M. tuberculosis        g                   a
Telente Genbank L05910 g                   a
      Consensus  CTG GGC CCC GGC GGT CTG TCC CGT
 Aerobic actino            g   t               a
       A. bovis               n
    A. viscosus
N. brasilensis     c   n       t         a   a g
N. brasilensis     c           t         a   a g
      N. otitis  a n ant n g nng   g          cc
    Rhodococcus    c   g   g       g   c   g   c
    Rhodococcus            g   t         ag    n
Corynebacterium    c               c   c       c
Corynebacterium        t   t               g   c
Corynebacterium        a           c   c   g   c
Proprionibacter        g       n
Proprionibacter        g
```

*FIG. 2G*

```
                              *
                                                    181
          M. nonchromo        g               a   t   t
          M. fortuitum                    t
          M. fortuitum                    t
          M. fortuitum                n   t
           M. chelonae    c               c
           M. chelonae    c     a n t a  n        n   g
             M. xenopi        g       g               t
           M. kansasii        t       g       a   g   t
        M. avium-inter        g           c       g
        M. avium-inter                                t
        M. avium-inter                                t
        M. avium-inter        g       g
        M. avium-inter                t   t       t
        M. avium-inter        g               a   g   t
              M. bovis        t       g     ... ... ...
       M. tuberculosis        t       g
       M. tuberculosis        t       g
       M. tuberculosis  n     t nn   nn n t          ..
       M. tuberculosis  n    nt t     g t n n
Telente Genbank L05910        t       g
             Consensus  GAG CGC GCC GGC CTG GAG GTC CGC
        Aerobic actino                    c      gn
              A. bovis              tc  a             t
           A. viscosus              tc  a
        N. brasilensis    a   g     a     c       g
        N. brasilensis    a   g     a     c       g
             N. otitis  a n n a       t   c  n
           Rhodococcus    a   g                       t
           Rhodococcus        t           c
       Corynebacterium    a       g     a c
       Corynebacterium                  a c   a   t   t
       Corynebacterium    c       g  cg a             a
       Proprionibacter    t           t a         g   a
       Proprionibacter    c             a         g   a
```

*FIG. 2H*

```
1941               FENLFF
cagacgctgT TGGAAAACTT GTTCTTCaag gagaagcgct acgacctggc ccgcgtcggt cgctataagg tcaacaagaa

2041
agcccatcac gtcgtcgacg ctgaccgaag aagacgtcgt ggccaccatc gaatatctgg tccgcttgca cgagggtcag

                                 DDIDHL
2141                             DDIDH
cggcgtcgag gtgccggtgg aaaccGACGA CATCGACCAC TTCggcaacc gccgcctgcg tacggtcggc gagctgatcc

                                              rpo 95
2241                                               rpo 105
atgtcgcgga tggagcgggt ggtccgggag cggatgaCCA CCCAGGACGT GGAGGCGATC ACACCGCAGA CGTtgatcaa
                                                                KY 290

2341
cgatcaagga gttcttcggc accagccagc tgagccaatt catggaccag aacaacccgc tgtcggggtt gacccacaag

                                                       rpo 293
2441                  rpo 273
gcccggcggt ctgtcACGTG AGCGTGCCGG GCTGGAGGTC CGCGACGTGC ACCCGTCGCA CTacggccgg atgtgcccga
                                  KY 292

2541                                          rpo 397
aacatcggtc tgatcggctc gctgtcggtg tacgcgcggG TCAACCCGTT CGGGTTCATC GAAACGccgt accgcaaggt

2641
acgagatcgt gtacctgacc gccgacgagg aggaccgcca cgtggtggca caggccaatt cgccgatcga tgcggacggt

2741
gctggtccgc cgcaaggcgg gcgaggtgga gtacgtgccc tcgtctgagg tggactacat ggacgtctcg ccccgccaga

2841                                                  NMQRQ(#1(#2)   2913
atgattccct tcctggagca cgacgacgcc aaccgtgccc tcatgggggc aAACATGCAG CGCCAGgcgg
```

FIG. 3A

```
                       2040
gctcgggctg catgtcggcg

                       2140
accacgatga ccgttccggg

                       2240
aaaaccagat ccgggtcggc

                       2340
catccggccg gtggtcgccg

                       2440
cgccgactgt cggcgctggg

                       2540
tcgaaacccc tgaggggccc

                       2640
ggtcgacggc gtggttagcg

                       2740
cgcttcgtcg agccgcgcgt

                       2840
tggtgtcggt ggccaccgcg
```

FIG. 3B

DETECTION OF A GENETIC LOCUS ENCODING RESISTANCE TO RIFAMPIN IN MYCOBACTERIAL CULTURES AND IN CLINICAL SPECIMENS

STATEMENT OF GOVERNMENT RIGHTS

This invention was made with Government support under Grant Nos. AI32403, AR41497, and AI30548 awarded by the National Institutes of Health. The Government has certain rights in the invention.

BACKGROUND OF THE INVENTION

After years of declining case rates, tuberculosis is again a major public health threat in the United States. Serious outbreaks involving patients infected with the human immunodeficiency virus (HIV) have occurred in several major metropolitan areas. Cases have also increased in other population groups, including the homeless, prisoners, migrant farm workers, immigrants, and health care workers.

Tuberculosis (TB) is a bacterial disease caused by organisms of the M. tuberculosis complex (i.e., M. tuberculosis (MTB), M. bovis and M. africanum). It is transmitted primarily by airborne droplets produced when individuals with pulmonary or laryngeal tuberculosis sneeze, cough, or speak. In the United States, the number of tuberculosis cases reported annually declined steadily between 1953 and 1985; however, in 1986 the rate for newly diagnosed cases began to increase, with a total of 26,283 cases were reported in 1991.

The antibiotic rifampin has long been an extremely effective antimicrobial agent and is one of the two major first-line anti-tuberculosis drugs. Rifampin has a unique site of action on the beta subunit (rpoB) of prokaryotic RNA polymerase, documented both biochemically (M. E. Levin et al., *Molec. Microbiol.,* 8, 277–285 (1993); F. G. Winder in *The Biology of the Mycobacterial,* Vol. 1, C. Ratledge et al., Eds., Academic Press: New York, pp. 353–438 (1982); and T. Yamada et al., *Antimicrob. Agents Chemother.,* 27, 921–924 (1985)), and genetically (D. J. Jin et al., *J. Molec. Biol.,* 202, 45–58 (1988); and N. Honoré et al., *Antimicrob. Agents Chemother.,* 37, 414–418 (1993)). Single site mutations in the gene for the beta subunit of RNA polymerase, rpoB, that confer rifampin resistance in Escherichia coil are well-characterized (Jin et al., *J. Mol. Biol.,* 202, 45–48 (1988)). Mutations conferring rifampin resistance in M. tuberculosis (Telenti et al., Lancet, 341, 647–650 (1993)), Mycobacterium leprae (Honoré et al., *Antimicrob. Agents Chemother.,* 37, 414–418 (1993)), and Mycobacterium srnegmatis (Levin et al., Mol. Microbiol., 8, 277–285 (1993)) have been similarly mapped to the same region in the sequence encoding the beta subunit of RNA polymerase. The ability of single base-pair mutations in the rpoB region to confer rapidly developing high-level resistance to rifampin in E. coil is consistent with the known high frequency of developing rifampin resistance in MTB (M. Tsukamura, Tubercle, 53, 111–117 (1972)). The increasing incidence of rifampin-resistant MTB strains make it imperative to determine clinical drug susceptibility immediately upon diagnosis of TB.

Since 1990, outbreaks of multi-drug resistant tuberculosis (MDR-TB) involving over 200 patients have been reported to the Centers for Disease Control (CDC). All these outbreaks were characterized by the transmission of strains of M. tuberculosis resistant to at least isoniazid and rifampin, with some strains showing additional resistance to other drugs including ethambutol, streptomycin, ethionamide, kanamycin, and rifabutin. As used herein, MDR-MTB refers the the multi-drug resistant strains of the organism, M. tuberculosis, and MDR-TB refers to the drug-resistant disease produced by the multi-drug resistant organism. Delays in the laboratory diagnosis and reporting of drug-resistant tuberculosis contributed to the magnitude of these outbreaks since cases were not rapidly identified, the organism was not isolated, or the patients were not put on adequate therapy.

A conclusive diagnosis of tuberculosis depends on the isolation and identification of the etiologic agent, Mycobacterium tuberculosis, which generally requires 3–8 weeks. Design of an appropriate therapeutic regimen depends on the results of subsequent antituberculosis susceptibility testing by the agar dilution method and produces additional delays of 3–6 weeks (Roberts et al., "Mycobacterium" in *Manual of Clinical Microbiology,* 5th Ed.; A. Balows et al., Eds.; American Society for Microbiology: Washington; pp. 304–339 (1991). Identification and drug resistance testing can now also be accomplished more quickly by using the BACTEC radiometric method. (Tenover et al., *J. Clin. Microbiol.,* 31,767–779 (1993) and Huebner et al., *J. Clin. Microbiol.,* 31,771–775 (1993)). Acid fast bacilli are detected in the BACTEC bottle, and an identification is made using a nucleic acid hybridization technique on the BACTEC-derived growth. Drug susceptiblity testing is then conducted using the same BACTEC growth to inoculate fresh BACTEC bottles containing various antituberculous drugs. This procedure reduces the time needed to generate a complete analysis, but the total time required to report susceptibility results for MTB is still typically in excess of 20 days. The need to minimize the transmission of newly identified multi-drug resistant strains of MTB requires the development of much more rapid identification procedures.

Since rifampin resistance in MTB correlates well with multi-drug resistance (Fischl et al., *Ann. Intern. Med.,* 117, 177–183 (1992); Frieden et al., *N. Engl. J. Med.,* 328, 521–526 (1993); Goble et al., *N. Engl. J. Med.,* 328, 527–532 (1993)), it can be used as a surrogate marker for MDR-MTB. Genotypic detection of multi-drug resistant MTB directly from clinical specimens is theoretically the fastest and most direct step toward determining effective therapy for patients infected with MDR-TB. A rapid test that could be performed directly on a patient specimen and that would both confirm a TB diagnosis and indicate whether it is a drug-resistant or drug-sensitive strain would be a major advance.

SUMMARY OF THE INVENTION

The present invention is directed to methods based on the polymerase chain reaction (PCR) for the detection of Mycobacterium tuberculosis (MTB) and concurrent determination of its drug susceptibility, utilizing the appropriate oligonucleotide primers. The methods are applicable to a wide variety of clinical and cultured specimens, and identify both resistant and non-resistant strains of MTB. The dual utility of the rpoB locus for both drug susceptibility and pathogen identification (MTB) may serve as a model for future rapid diagnostic methods development.

This invention involves a comparative analysis of the rpoB sequences in MTB, other mycobacteria and related GC-rich bacteria (FIG. 1) demonstrating the heretofore undiscovered presence of a set of MTB-specific position-specific "signature nucleotides" that permits unequivocal identification of MTB strains, both drug-resistant and drug-sensitive. Utilization of this information in connection with sequencing the appropriate region on the rpoB gene can yield a positive identification of MTB along with essential information about its drug resistance phenotype. This invention therefore further relates to the use in polymerase chain reactions (PCR) of particular oligonucleotide primers (Table 2) of varying levels of specificity: degenerate primers for all bacterial rpoB gene sequences; intermediate specificity primers for mycobacterial rpoB genes and rpoB genes from other GC-rich bacteria; and high specificity primers specific for the MTB rpoB gene. This invention also relates to the use of PCR and methods such as automated DNA sequencing, reverse dot blotting, microtytre plate oligonucleotide capture, single stranded conformational polymorphisms, dideoxy fingerprinting, and the like, to identify MTB and predict rifampin susceptibility directly from clinical specimens.

Accordingly, this invention provides a rapid, sensitive and specific process for detecting in vitro the presence of Mycobacterium tuberculosis and its drug-resistance phenotype. In accordance with the invention, the identification of M. tuberculosis involves the detection of all or some signature nucleotides in the rpoB gene of mycobacterium tuberculosis. The invention provides for the determination of rifampin resistance by detection of mutations in the rpoB gene of M. tuberculosis, particularly with respect to the nucleotide sequence of that same rpoB gene in mycobacterium tuberculosis that are not resistant to rifampin. Rifampin resistance is correlated with resistance to other drugs, thus this invention provides a means of detecting multi-drug resistant M. tuberculosis.

The invention utilizes polymerase chain reaction (PCR) to effect the determination of M. tuberculosis identity and drug susceptibility phenotype. This process comprises steps of isolation and purification of target DNA from bacterial cultures with clinical samples, and amplifying regions of the rpoB gene using specific oligonucleotide primers described herein. Amplified DNA is isolated and processed such that the sequence of nucleotides is determined. Inspection of the nucleotide sequence yields the useful information concerning organism identity and drug-susceptibility phenotype.

The PCR-based methods of the present invention are direct methods for the detection of M. tuberculosis DNA in a variety of biological samples, particularly human biological samples, e.g., fluid samples and tissue samples. The methods of the present invention are particularly advantageous because they have proven clinical value. That is, they show greater than 90% sensitivity and greater than 90% specificity, and often greater than 95% sensitivity and 100% specificity.

One method of the present invention for detecting M. tuberculosis in a biological sample using PCR includes the steps of: isolating DNA from the biological sample; amplifying the isolated DNA under hybridizing conditions with a primer set that targets portions of the gene encoding rpoB; wherein the pimer set comprises at least one primer that hybridizes under hybridizing conditions to a nucleotide sequence containing at least one signature nucleotide for M. tuberculosis; and isolating and analyzing the amplified DNA to determine the presence of M. tuberculosis, specific signature sequences, or significant mutations. Preferably, the method detects M. tuberculosis that is resistant to rifampin. More preferably, the method detects M. tuberculosis that is resistant to rifampin and at least one other antibiotic, i.e., multi-drug resistant-MTB.

The methods of the present invention use standard PCR techniques, preferably including single-tube hemi-nesting procedures as described herein for improving sensitivity and specificity. The primer sets used include at least one primer that hybridizes to a nucleotide sequence containing at least one signature nucleotide for M. tuberculosis, eleven of which are shown herein (FIG. 2). Preferably, the signature nucleotide is contained within 5 nucleotides of the 3' end of the primer. More preferably, the signature nucleotide is the last nucleotide at the 3' end of the primer. Most preferably, such primers substantially correspond to a primer selected from the group consisting of rpo105, rpo273, KY290, and KY292, the sequences of which are shown in Table 2. Of these, rpo105 and rpo273 are the most highly specific for the MTB rpoB gene, and are therefor particularly preferred in the methods of the present invention. As used herein, "substantially corresponding to" means that the primer sequence of interest has at least about 50%, preferably at least about 80%, sequence identity with the referenced primer sequence. The PCR method preferably includes amplification by a primer that is less specific than primers rpo105, rpo273, ky290, and ky292. These include primers that substantially correspond to a primer selected from the group consisting of rpo95, rpo293, and rpo397, the sequences of which are shown in Table 2. It should be noted that these sequences of intermediate specificity have a restriction site and 2–4 miscellaneous bases at the 5' end that do not necessarily hybridize to the rpoB gene.

Additionally, if desired, even less specific primers can be used in the method of the present invention. These primers are derived from an AT-rich portion of the bacterial gene encoding rpoB. This AT-rich portion encodes a highly conserved amino acid sequence. Preferably, these primers hybridize to the rpoB gene in regions delineated by nucleotides 1945–1980, 2155–2190, and 2885–2910, as shown in FIG. 3 (SEQ ID NO:1). As used herein, "highly conserved" means that these portions of the amino acid sequence have at least about 75% sequence identity among all species analyzed to date.

All primers used in the methods of the present invention have at least 14 nucleotides, preferably about 14–75, more preferably about 14–50, and most preferably about 15–30 nucleotides. The hybridizing and amplification conditions used in the present invention include an annealing temperature of about 60°–75° C., an extension temperature of about 70°–90° C., and a denaturation temperature of about 90°–100° C. for a total of about 30–50 cycles in a PCR mix containing a sufficient amount of buffer to maintain the pH at 8–8.5, and a sufficient amount of each of the following reagents to maintain: a final concentration of 50–200 micromolar or each dNTP; a final concentration of 0.1–2 micromolar primer; a final volume-% of 5–15% glycerol; and about 0.1–1 Unit of AmpliTaq per 50 microliters of the total volume of the reaction mixture.

DETAILED DESCRIPTION OF THE INVENTION

Figure 1:
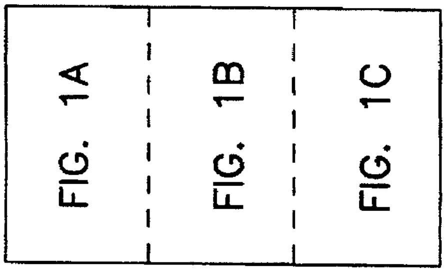
FIG. 1. Alignment of a portion of amino acid sequences for the beta subunit of RNA polymerase (rpoB) from Mycobacterium leprae, Mycobacterium tuberculosis, Escherichia coil, S. typhimurium and P. putida. Underlined residues (FENLFF, DDIDHL and NMQRQ) indicate regions that are highly conserved within the bacterial kingdom and that were used in the development of the degenerate primers listed in Table 2. The numbering system is arbitrary and assigned by the GCG software.

Polymerase chain reaction (PCR), an extremely rapid and sensitive method of detecting and amplifying DNA, is finding increasing use in genotypic detection of drug resistance as mechanisms of drug resistance become elucidated (Finken et al., *Molecular Microbiol.*, 9, 1239–1246, (1993); J. J. Goswitz et al., *Antimicrob. Agents Chemother.*, 36, 1166–1169 (1992); Y. Zhang et al., *Nature*, 358, 591–593 (1992)). It forms the basis of the method of the present invention for direct detection of M. tuberculosis and its drug susceptibility.

Rifampin is a bacterial drug which is particularly potent against the tuberculosis group of mycobacteria—Mycobacterium tuberculosis, M. bovis, and M. africanum—and, in consequence, it has been particularly effective in the treatment of tuberculosis. Standard anti-tuberculosis regimens generally include INH rifampin, or isoniazid, often in combination with the weaker drugs pyrazinamide, ethambutol, or streptomycin. Besides its use in therapy, rifampin is also given to close contacts of patients as a prophylactic measure.

The sequences of the rpoB genes for various organisms that are included in the alignment were derived by standard sequence techniques. The base sequences of the nucleotides are written in the 5'→3' direction. Each of the letters shown is a conventional designation for the following nucleotides: A—Adenine; G—Guanine; T—Thymine; and C—Cytosine. The oligonucleotide primer sequences included as part of the invention can be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

The nucleotide sequences of the invention are in a purified form. For instance, the nucleotides are free of human blood-derived proteins, human serum proteins, viral proteins, nucleotide sequences encoding these proteins, human tissue, and human tissue components. In addition, it is preferred that the nucleotides are free of other nucleic acids, extraneous proteins and lipids, and adventitious microorganisms, such as bacteria and viruses.

This invention includes variants of the nucleotide sequences of the invention exhibiting the same selective hybridization properties as the oligonucleotide primers identified herein. The nucleotide sequences of the present invention can be employed in PCR which is advantageous because this technique is rapid and sensitive.

DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the target DNA. The PCR reaction mixture can contain the target DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the target DNA at an elevated temperature, cooling of the reaction mixture, and polymerization with the DNA polymerase.

Single-strand conformation polymorphism (SSCP) analysis can be used to detect DNA polymorphisms and point mutations in a variety of positions in amplified DNA fragments. Alternatively, a portion of the PCR reaction mixture can be separated and subjected to hybridization with an end-labeled nucleotide probe, such as a $^{32}P$ labeled adenosine triphosphate end-labeled probe. The amplified product can be isolated and sequenced to obtain information at the nucleotide level.

Since it may be possible to increase the sensitivity of detection by using RNA instead of chromosomal DNA as the original template, this invention contemplates using RNA sequences that are complementary to the DNA sequences described herein. The RNA can be converted to complementary DNA with reverse transcriptase and then subjected to DNA amplification.

The following examples are offered to further illustrate the various specific and preferred embodiments and techniques. It should be understood, however, that many variations and modifications may be made while remaining within the spirit and scope of the present invention.

EXPERIMENTAL EXAMPLES

EXAMPLE 1

Correlation of Rifampin Resistance with Multi-drug Resistance in M. tuberculosis

TABLE 1

Rifampin resistance patterns among 83 drug-resistant *M. tuberculosis* isolates from 1/1/90–12/31/92, Mayo Clinic Mycobacteriology Laboratory (Total n = 787).

| Resistance[1]-to: | Rifampin resistant/ Total resistant | Percent |
|---|---|---|
| 1 drug | 7/54 | 13 |
| 2 drugs | 3/10 | 30 |
| 3 drugs | 8/9 | 89 |

TABLE 1-continued

Rifampin resistance patterns among 83 drug-resistant *M. tuberculosis* isolates from 1/1/90–12/31/92, Mayo Clinic Mycobacteriology Laboratory (Total n = 787).

| Resistance[1]-to: | Rifampin resistant/ Total resistant | Percent |
|---|---|---|
| 4 drugs | 4/5 | 80 |
| 5 drugs | 5/5 | 100 |

[1]Resistance is defined as growth of more than 1% of a ca. 200-cfu inoculum after 2 wk incubation at 35° C. in air on Middlebrook 7H11 agar containing one of the following drugs (concentrations, μg/mL, in parentheses): Isoniazid (4), rifampin (4), streptomycin (16), ethambutol (8), pyrazinamide (32) (Dimed Inc., St. Paul, MN).

EXAMPLE 2

Detection of Rifampin Resistance in Mycobacterial Cultures and Clinical Specimens Using Oligonucleotide Primers DDIDHL, NMQRQ, rpo95, rpo293 and rpo397

Oligonucleotide primers DDIDHL, NMQRQ(#1), rpo95, rpo293 and rpo397 (Table 2) were used to amplify rpoB deoxyribonucleic acid (DNA) from bacterial cultures and clinical isolates using the methods and producing the results described below.

TABLE 2

LIST OF PRIMERS

| Primer Name | Sequence | Length |
|---|---|---|
| DDIDHL[1] | 5' TTG AAT TCG A(CT)G A(CT)A T(ACT)G A(CT)C A(CT)C T 3' | 25-mer |
| DDIDH[2] | 5' GTC CCT GCA GGA CGA CAT CGA CCA C 3' (SEQ ID NO: 3) | 25-mer |
| NMQRQ (#1)[3] | 5' TTG GAT CC(CT) TG(AGC) CG(CT) TGC AT(AG) TT 3' (SEQ ID NO: 4) | 23-mer |
| NMQRQ (#2)[4] | 5' GGG ATC CGC (TC)TG CG(CT) TGC ATG TT 3' (SEQ ID NO: 5) | 23-mer |
| FENLFF[5] | 5' CCC TGC AGT TCG AGA ACC TGT TCT TC 3' (SEQ ID NO: 6) | 26-mer |
| rpo95 | 5' CCA CCC AGG ACG TGG AGG CGA TCA CAC 3' (SEQ ID NO: 7) | 27-mer |
| rpo293 | 5' AGT GCG ACG GGT GCA CGT CGC GGA CCT 3' (SEQ ID NO: 8) | 27-mer |
| rpo397 | 5' CGT TTC GAT GAA CCC GAA CGG GTT GAC 3' (SEQ ID NO: 9) | 27-mer |
| rpo105 | 5' CGT GGA GGC GAT CAC ACC GCA GAC GT 3' (SEQ ID NO: 10) | 26-mer |
| rpo273 | 5' GAC CTC CAG CCC GGC ACG CTC ACG T 3' (SEQ ID NO: 11) | 25-mer |
| KY290 | 5' GGC GAT CAC ACC GCA GAC GT 3' (SEQ ID NO: 12) | 20-mer |
| KY292 | 5' GGA CCT CCA GCC CGG CA 3' (SEQ ID NO: 13) | 17-mer |

[1]The first eight bases comprise a nonhybridizing tail consisting of two (TT) filler bases followed by GAATTC, a restriction site for EcoR1 restriction enzyme incorporated to facilitate cloning using the amplicon at a later date, if desired. The remaining bases hybridize to bacterial rpoB DNA

[2]The first ten bases comprise a nonhybridizing tail consisting of four filler bases (GTCC) followed by CTGCAG, a restriction site for pst1 restriction enzyme incorporated to facilitate cloning using the amplicon at a later date, if desired. The remaining bases hybridize to bacterial rpoB DNA.

[3]The first several bases comprise a nonhybridizing tail consisting of filler bases followed by a restriction site for incorporated to facilitate cloning using the amplicon at a later date, if desired. The remaining bases hybridize to bacterial rpoB DNA.

[4]The first several bases comprise a nonhybridizing tail consisting of filler bases and a restriction site to facilitate cloning using the amplicon at a later date, if desired. The remaining bases hybridize to bacterial rpoB DNA.

[5]The first eight bases comprise a nonhybridizing tail consisting of two filler bases (CC) followed by CTGCAG, a restriction site for pst1 restriction enzyme incorporated to facilitate cloning using the amplicon at a later date, if desired. The remaining bases hybridize to bacterial rpoB DNA.

A. Clinical isolates and reference strains. Reference strains (Table 3) were obtained from the American Type Culture Collection (ATCC) and propogated using standard laboratory methods. Clinical specimen sources for bacteria were isolated and identified as part of routine clinical laboratary processing of such specimens. Susceptibility to rifampin and other anti-mycobacterial antibiotics was determined by the 1% proportion method as defined by G. D. Roberts et al. *Manual of Clinical Microbiology,* 5th Edition; A. Balows et al., Eds.; American Society for Microbiology: Washington, D.C.; pp. 304–339 (1991) (incorporated herein by reference). Resistance to rifampin was defined as >1% growth of a standard inoculum on Middlebrook 7H10 agar containing 4 μg/mL rifampin (Dimed, St. Paul, Minn.).

TABLE 3

Amplification of the rpoB locus from a panel of bacterial DNAs using PCR primers rpo95 and rpo293

| Mycobacteria: | rpoB Amplified |
|---|---|
| *M. avium* complex | yes |
| *M. fortuitum* | yes |
| *M. marinum* | yes |
| *M. phlei* | yes |
| *M. smegmatis* | yes |
| *M. triviale* | yes |
| *M. tuberculosis* | yes |
| *M. xenopi* | no |

TABLE 3-continued

Amplification of the rpoB locus from a panel of bacterial DNAs using PCR primers rpo95 and rpo293

| Mycobacteria: | rpoB Amplified |
|---|---|
| Other GC-rich Bacteria: | |
| Actinomyces sp. | yes |
| Corynebacterium sp. | yes |
| Rhodococcus sp. | yes |
| Streptomyces sp | yes |
| Other Bacteria: | |
| *Haemophilus influenzae* | no[1] |
| Nesseria sp. (3 isolates) | no |
| Staphylococcus sp. | no |
| Streptococcus sp. (6 isolates) | no |
| Peptostreptococcus sp. | no |
| Veillonella sp. | no |
| Lactobacillus sp. | no |

[1]The first isolate tested was probe-positive, but a second isolate was negative. The initial result was judged to be a false positive.

B. Bacterial DNA isolation. DNA from cultured isolates of bacteria and mycobacteria was prepared for polymerase chain reaction (PCR) amplification by either the bead-beat/boil (BBIB) method or by bead-beat/phenol (BB/P) extraction. For the BB/B method, a 10-µL loopful of each isolate was harvested and placed in a 2.0-ml screw cap microcentrifuge tube (Sarstedt, Inc.) filled ⅔ full with 0.1 mm diameter zirconium beads (Biospec Products, Bartlesville, Okla.) and 1.0 mL lysis buffer (lysis buffer: 10 mM Tris (hydroxymethyl)aminomethane hydorchloride (Tris-HCl), pH 8.0, 1 mM ethylenediaminetetraacetic acid (EDTA), 1% Triton-X100 (all from Sigma Chemical Company, St. Louis, Mo.)). Tubes were oscillated on a Mini Bead Beater (Biospec Products, Bartlesville, Okla.) for 30 seconds. The supernatant was pipetted into a clean tube, boiled 30 minutes to kill the bacteria, and stored at −20° C. Two µL was used as PCR target in 50-1µL PCR reactions. For the BB/P extraction method, a 10-µL loopful of the isolate was placed in a 300-µL volume of phenol, equilibrated with TE buffer (TE buffer: 10 mM Tris-HCl, pH 8.0, 1 mM EDTA), in a 300-µL screw cap microcentrifuge tube (Sarstedt, Inc.) ⅔ filled with 0.1-mm diameter zirconium beads, 150 µL TE buffer was added, and the mixture was oscillated 30 seconds on a Mini Bead Beater. The tubes were incubated 30 minutes at 25° C. to kill bacteria before being centrifuged for 20 seconds in a microcentrifuge to separate phases. The aqueous phases were pipetted into clean tubes and stored at −20° C. Purified DNA was extracted from the aqueous phases by using Isoquick nucleic acid extraction kit reagents (Microprobe, Garden Grove, Calif. 92641). Five µL of 1/10 or 1/100 dilutions of purified DNA in water was used as target in all PCR reactions.

C. DNA extraction from clinical specimens. Clinical specimens (respiratory: sputum, bronchial wash; non-respiratory: urine) were processed by 1% NaOH (Sigma Chemical Company, St. Louis, Mo.) liquefaction-decontamination and sedimentation, and 0.5 ml of sediments were inoculated into 7H10, Selective 7H11, and Bactec 12B media (see G. D. Roberts et al., "Mycobacterium", in *Manual Of Clinical Microbiology,* 5th Edition; A. Balows et al., Eds.; American Society for Microbiology: Washington; pp. 304–339 (1991)). DNA was isolated from 1.0 ml of the residual sediment by centrifugation for 15 minutes in microcentrifuge tubes; the supernatant was subsequently removed and discarded. Zirconium beads (0.1 mm diameter) were added to ⅔ tube volume, and 600 µL phenol plus 400 µL TE buffer were added, and the screw-capped tube subjected to bead-beating for 30 seconds followed by a 15 minute incubation at 25° C. to kill organisms, and 3 minutes centrifugation at 16000×g in a microcentrifuge to separate the phases. The aqueous phase was transferred to clean tubes and stored at −20° C. DNA was further extracted from the aqueous phases by using the Isoquick DNA extraction kit. Five µL of 1/10 or 1/100 dilutions of purified DNA in water were used as target in PCR reactions.

Figure 2:
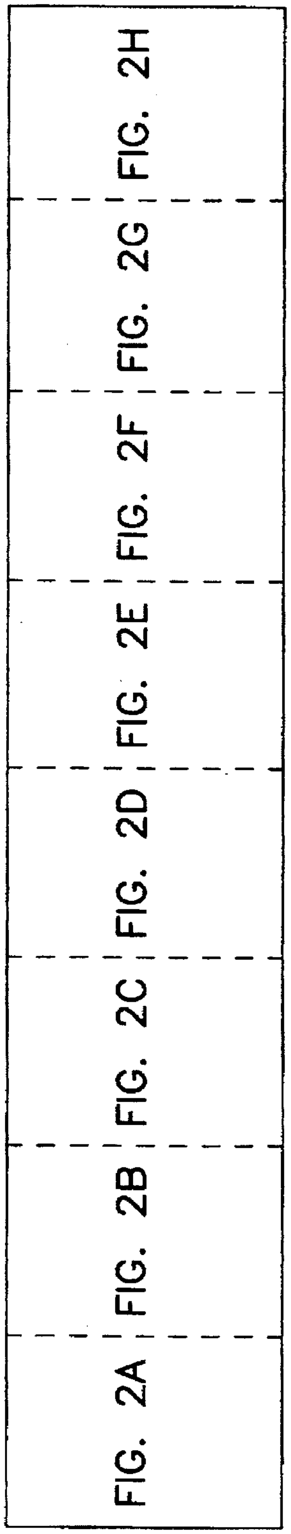
FIG. 2. Alignment of a portion of rpoB DNA sequences from M. tuberculosis and other GC-rich bacteria. Base numbering system is that of L. P. Miller et al. for the entire 3533 base pair rpoB gene, GenBank accession number L27989 (1994). Lower-case nucleotides indicate those differing from the consensus sequence. A dot (.) indicates that there was no DNA sequence to be read at that position. The letter (N) in the consensus sequence indicates that the automated sequencer could not identify the base at that position, and a hyphen (-) indicates a gap in the sequence. Positions of MTB position-specific "signature nucleotides" at base numbers 2312–2313 (129–130), 2373–2374 (190–191), 2378 (195), 2408–2409 (225–226), 2426 (243), 2441 (258), 2456 (273) and 2465 (282), are indicated at the top of the figure by an asterisk (*). Numbers in parenthesis are the corresponding base pair numbers according to the numbering system of Telenti et al., Lancet, 34, 647–650 (1993), Genbank Accession Number L05910. For those strains having several different entries in the figure, each entry represents a distinct patient sample.

D. Design of sequence degenerate primers DDIDHL and NMQRQ. Oligonucleotide primers DDIDHL and NMQRQ (Table 2) were designed to hybridize to portions of the rpoB gene that are highly conserved within the bacterial kingdom (FIG. 1). The amino acid sequence alignment in FIG. 1 was created using the Pileup utility of Genetics Computer Group (Madison, Wisc.). DDIDHL is named for the highly conserved bacterial rpoB amino acid sequence aspartate(D)-aspartate(D)-isoleucine(I)-aspartate(D)-histidine(H)-leucine(L) (SEQ ID NO:14) (e.g. amino acids #442–448 in the rpoB protein from M. tuberculosis), and NMQRQ is named for the highly conserved amino acid sequence asparagine(N)-methionine(M)-glutamine(Q)(SEQ ID NO:15)-arginine(R)-glutamine(Q) (e.g. amino acids #684–688 in the rpoB protein from M. tuberculosis) (FIG. 2). Degenerate nucleotides were chosen such that the same amino acid is encoded at every position (using different three-nucleotide codons). These regions were ideally suited to rpoB-specific priming because they contain AT-rich codons in a genome that is otherwise rich in GC base pairs. DDIDHL and NMQRQ were intended to amplify most bacterial rpoB gene sequences.

E. Polymerase chain reactions. Primers DDIDHL, NMQRQ, rpo95, rpo293 and rpo397 (Table 2) were synthesized on an ABI Model 394 Synthesizer (Applied Biosystems, Inc., Foster City, Calif.). PCR reactions (50 µL) contained target DNA (5 µL), 1 µM primers, 10% glycerol (Sigma Chemical Company, St. Louis, Mo.), 2 mM $MgCl_2$ (Sigma Chemical Company, St. Louis, Mo.), 0.2 mM each deoxyadenosine triphosphate (dATP), deoxyguanidine triphosphate (dGTP), deoxycytidine triphosphate (dCTP), and deoxyuridine triphosphate (dUTP) (all nucleoside triphosphatases (dNTPs) from Boehringer Mannhelm Biochemicals, Indianapolis, Ind.), 1.25 unit AmpliTaq polymerase (Perkin-Elmer Cetus, Norwalk, Conn.), and 1X Perkin-Elmer Cetus PCR buffer II. Either a Temptronic Series 669 (Barnstead-Thermolyne, Dubuque, Iowa 52004) or Perkin-Elmer Cetus Model 9600 thermal cycler was used with identical cycling parameters. Amplification with DDIDHL (upstream) and NMQRQ (downstream) was accomplished using 40 cycles of 94° C. (1 minute) and 55° C. (1 minute), and 72° C. (3 min), after an initial 4 minutes at 94° C. to denature input DNA, with a final 5 minutes at 72° C. for strand extension. Amplification with upstream primer rpo95 and either downstream primer rpo293 (producing a 224 base pair amplicon) or rpo397 (producing a 328 base pair amplicon) was done using 50 cycles of 94° C. (1 minute) and 65° C. (1 minute), after an initial 4 minute at 94° C. to denature input DNA, with a final 4 minute at 72° C. for strand extension. Amplification products were detected by agarose gel electrophoresis of 1/5 or 1/10 of the reaction mixture in 2% agarose (Seakem GTG, FMC, Rockland, Me.) made up in 1× Tris-borate-EDTA (TBE) (0.089M Tris-borate, 0.089M boric acid, 2 mM EDTA), followed by staining with ethidium bromide. The products were purified by using Magic PCR Prep kit reagents (Promega, Madison, Wisc.), and sequenced by using primer rpo95 at the Mayo Clinic Molecular Biology Core Facility using an Applied Biosystems 373A automated sequencer and the dye-coupled dideoxyribonucleotide cycle sequencing method (Applied Biosystems Inc. Foster City, Calif.). Sequencing reactions were run using 5% (v/v) dimethylsulfoxide for twenty-five cycles of 96° C. (30 seconds), 50° C. (15 seconds), 60° C. (4 minutes). To provide additional detection sensitivity, Southern blots of agarose gels were prepared on nylon membranes (Nytran, #77593, Schleicher and Schuell, Keene NH) by overnight capillary blotting followed by UV-crosslinking. The blots were probed with a 328-bp MTB rpoB amplification product of primers rpo95 and rpo397 which was directly coupled with horseradish peroxidase using ECL kit reagents according to the manufacturer's recommendations (Amersham, Arlington Heights, Ill.). Hybridization conditions (42° C., 16 hours) specified by the kit manufacturer were used. Chemiluminescence was detected by exposure of Kodak AR X-ray film for 5 minutes.

F. PCR Results. A PCR product of the expected size, ca. 700 base pair, was obtained after amplification of genomic target DNA extracted from E. coil and two MTB isolates, one resistant and one susceptible to rifampin. The more specific primers rpo95, rpo293 and rpo397 amplified reference mycobacterial rpoB gene sequences, including both resistant and non-resistant MTB but excluding M. xenopi, and rpoB DNA from other GC-rich organisms, but not rpoB from other bacteria (Table 3). Clinical results, reported in Table 4 showed that identification and drug susceptibility phenotype obtained directly by sequencing the PCR product confirmed the results of acid-fast testing, culture, and actual drug susceptibility testing.

EXAMPLE 3

Identification of MTB position-specific signature nucleotides

DNA sequences obtained through the use of the rpo95/rpo293 and rpo95/rpo397 primer pairs described in Example 2 were aligned using the GCG nucleic acid analysis software (Genetics Computer Group, Madison Wisc.) running on a VAX computer in the Mayo Clinic/Foundation Research Computing Facility (FIG. 2). Nucleotides were numbered with reference to the 432-bp M. tuberculosis rpoB region sequenced by Telente et al., Lancet, 341, 647–650 (1993) (incorporated herein by reference). The GCG Pileup utility was used to generate the sequence alignments, using default parameters when options were available. The results of the Pileup analyses were used as input for the GCG Pretty utility. Pretty generated a consensus sequence and displayed only nucleotides that differed from the consensus strand. It was found upon inspection of the sequence alignment that there were eleven sites (positions 129–130, 190–191, 195, 225–226, 243, 258,273 and 282) at which the nucleotide observed for Mycobacterium tuberculosis (MTB) differed from all or most related organisms (Table 5). A combination of all or some of these bases (the "signature" nucleotides, defined as G129, T130, A190, G191, A195, G225, T226, A243, G258, A273, and T282) was unique to MTB and common to 60+MTB strains sequenced. This was true regardless of whether the MTB strain was resistant or sensitive to rifampin, as the mutations that lead to rifampin resistance occur at other locations. Telente et al., Lancet, 341, 647–650 (1993)

TABLE 4

Summary of rpoB PCR results with 16 clinical specimens

| | | Acid-fast | | Signature | Rifampin Phenotype of Isolate | |
|---|---|---|---|---|---|---|
| Specimen | Source | Smear[1] | Culture[2] | Sequence[3] | Predicted[4] | Actual[5] |
| 1 | Sputum | + (many) | MTB | MTB | Rif-S | Rif-S |
| 2 | Sputum | — | — | — | | |
| 3 | Sputum | +? (rare) | — | Ambiguous | | |
| 4 | Sputum | — | — | — | | |
| 5 | Urine | — | — | — | | |
| 6 | Sputum | + (rare) | MAC | Ambiguous | | |
| 7 | Sputum | — | — | — | | |
| 8 | Tr. Sec.[6] | — | — | — | | |
| 9 | Br. Wash | — | MTB | — | | |
| 10 | Sputum | — | — | — | | |
| 11 | Sputum | + (many) | MTB | MTB | Rif-S | Rif-S |
| 12 | Sputum | — | MAC | — | | |
| 13 | Sputum | — | MTB | MTB | Rif-S | Rif-S |
| 14 | Sputum | — | — | — | | |
| 15 | Sputum | — | MTB | MTB | Rif-S | Rif-S |
| 16 | Sputum | + (many) | MTB | MTB | Rif-R | Rif-R |

[1]Smears stained with auramine-rhodamine (Truant's) reagents and screened microscopically at 250X. Quantitation is Negative (0/smear), Positive rare (3–9/smear), Positive few (>10/smear), or Positive many (>1/microscope field).
[2]Negative culture results means no growth after 60 days. MAC is *Myobacteria avium-intracellulare*
[3]Amplification products were sequenced only if a signal was seen on a Southern blot. Identification of MTB was based on occurrence of specific MTB-specific signature sequences at positions indicated in Example 3 (Table 5). A (—) indicates that no PCR product was detected after amplification. Amplification was done with rpo95 upstream and rpo293 (for specimen nos. 1–12) or rpo397 (for specimen nos. 13–16) downstream.
[4]Prediction of rifampin phenotype as sensitive (Rif-S) or resistant (Rif-R) was based on analysis of amplified rpoB DNA sequences directly from the clinical specimens.
[5]Susceptibility determined by agar dilution. The MDR-MTB isolate from specimen no. 16 was resistant to cycloserine, ethambutol, pyrazinamide, and rifampin.
[6]Tracheal secretions.

Specifically, as shown in FIG. 1 of Telenti et al. (Lancet, 341, 647–650 (1993)), the fifteen mutations identified in rifampin-resistant M. tuberculosis were found to involve eight conserved amino acids clustered within a 23 amino acid RNA polymerase region encoded by rpoB. This highly mutated region spans nucleotides 187 (2370) through 255 (2438), representing codens 511 through 533. Nucleotide numbering as used in this paragaph is based on the Telenti et al. numbering system, GenBank accession number L05910; numbers in parentheses are based on the numbering system of L. P. Miller et al., for the entire rpoB gene sequence, GenBank accession No. L27989. The codon numbering is based on the E. coli RNA polymerase amino acid numbering system. Within this region, specific sites having point mutations associated with rifampin resistance include nucleotide positions 188, 194, 203: 221, 232, 233, 234, 247, 248 and 254 (Telenti et al. numbering system, GenBank accession number L05910).

TABLE 5

Position-specific signature nucleotides within the rpoB gene of *M. tuberculosis*

| Nucleotide[1] Position | MTB Signature[2] | Exceptions (same base or base pair as MTB)[3] |
|---|---|---|
| 129–130 (2312–2313) | gac GT tga | *M. bovis* |
| 190–191 (2373–2374) | ctg AG cca | Actinomyces sp., *M. aurum*, *M. bovis* |
| 195 (2378) | cca A ttc | *M. bovis* |
| 225–226 (2408–2409) | ggg GT tga | *M. triviale*, *M. bovis* |
| 243 (2426) | ccg A ctg | *M. bovis* |
| 258 (2441) | ggg G ccc | *M. triviale*, *M. marinum*, *M. kansasii*, Nocardia sp., propionibacter sp., rhodococcus sp. |
| 273 (2456) | gtc A cgt | *M. bovis* |
| 282 (2465) | gcg T gcc | *M. kansasii*, *M. bovis* |

[1]Nucleotide numbering based on Telente et al., Lancet, 341, 647–650 (1993). Numbers in parentheses are based on the numbering system of L.P. Miller et al., for the entire rpoB gene sequence GenBank accession No. L27989.
[2]MTB signature bases (capital letters) are not altered in rifampin-resistant MTB.
[3]Differences in nucleotide sequence at other locations are also present.

EXAMPLE 4

Design of Oligonucleotide Primers rpo105, rpo273, KY290 and KY292 Showing High Specificity for MTB Oligonucleotide primers specific for MTB (rpo105/rpo273 and KY290/KY292) (Table 2) were designed by making the 3' end complement and terminate at one of the newly identified unique positions (in the case of the upstream primers rpo105 and KY290, the 3' end is at site 130; in the case of downstream primer rpo273, it is at site 273, and in the case of downstream primer KY292, it is at position 282) (FIG. 3) (SEQ ID NO:1). The remaining composition of the primers was based on direct complementarity to the MTB rpoB sequence, and the optimum length was determined with the aid of computer-generated thermal profiles (OLIGO Primer Analysis Software version 4.0 for the Macintosh, National Biosciences, Inc. Plymouth, Minn.).

EXAMPLE 5 pCR using Primers KY290 and KY292

PCR using primer pair KY290/KY292 was conducted using target DNA from several mycobacterial reference strains. Strains M. scrofulaceum (ATCC#19981), M. smegmatis (ATCC#14468), M. simiae (ATCC#25275), M. xenopi (ATCC#19250), M. brunense (ATCC#23434) and M. chelonae (ATCC#35752) were obtained from the American Type Culture Collection. The other isolates were gifts from collaborator laboratories in Europe and identified in those laboratories. Isolation and purification of bacterial DNA was performed according to standard methodology. A general method for the isolation of mycobacterial DNA can be found in Patel et al., *Journal of General Microbiology,* 132, 541–551 (1986). Oligonucleotide primers were synthesized using standard methodology. Methods of preparing oligonucleotides of specific sequence are known in the art, and include, for example, cloning and restriction of appropriate sequences, and direct chemical synthesis by a method such as the phoshotriester method of Narange et al., *Meth. Enzymol.,* 68, 90–99 (1979); the phosphodiester method of Brown et al., *Meth. Enzymol.,* 68, 109–151 (1979); the diethylphosphoramidite method of Beaucage et al., Tetrahedron Lett., 22, 1859–1862 (1981); and the solid support method of U.S. Pat. No. 4,458,066, each incorporated herein by reference. A review of synthesis methods is provided in Goodchild, *Bioconjugate Chemistry,* 1, 165–187 (1990), incorporated herein by reference.

Primer pairs analyzed were rpo95/KY292 and KY290/KY292. PCR reactions (100 μl) contained target bacterial DNA (5 μl), 50 mM Tris-HCl, pH 8.9, 50 mM KCl, 10% glycerol (Sigma Chemical Company, St. Louis, Mo.), 500 nM each primer, 2 mM $MgCl_2$ (Perkin-Elmer-Cetus, Norwalk, Conn.), 0.2 mM each deoxyadenosine triphosphate (dATP), deoxyguanidine triphosphate (dGTP), deoxycytidine triphospate (dCTP) and deoxythymidine triphosphate (dTTP) (i.e. dNTP, where "N" refers to A,G,C or T, (Perkin-Elmer-Cetus)), 3 units Taq polymerase (Perkin-Elmer-Cetus), and 1 unit uracil-N-glycosylase (Perkin-Elmer-Cetus). Thermal cycling was performed using a GeneAmp PCR System 9600 (Perkin-Elmer-Cetus). Conditions for amplification comprised an initial 50° C. incubation for 2 min, followed by 2 cycles of [98° C. (20 sec), 62° C. (20 sec) 72° C. (45 sec)] and 35 cycles of [94° C. (20 sec), 62° C. (20 sec) 72° C. (45 sec)], followed by a final 72° C. incubation for at least 10 min for strand extension. Amplification products were analyzed by gel electrophoresis on 2% Nusiev/0.5% agarose gels (FMC Products, Rockland, Me.) in a Tris-Borate-EDTA buffer (composed as described in Sambrook et al., Molecular Cloning Manual) (incorporated herein by reference) and stained with ethidium bromide.

Primer pair KY290/KY292 amplified only M. tuberculosis and M. chelonae, whereas primer pair rpo95/KY292 amplified M. kansasii as well. Both pairs were highly sensitive, amplifying MTB DNA at the 100 fg level.

TABLE 6

Specificity of primer pairs rpo95/KY292 and KY290/KY292[1]

| Mycobacterial species tested | rpo95/KY292 | KY290/KY292 |
|---|---|---|
| *M. tuberculosis* | + | + |
| *M. scrofulaceum* | – | – |
| *M. fortuitum* | – | – |
| *M. avium* | – | – |
| *M. kansasii* | + | – |
| *M. intracellulare* | – | – |
| *M. phlei* | – | – |
| *M. smegmatis* | – | – |

TABLE 6-continued

Specificity of primer pairs rpo95/KY292 and KY290/KY292[1]

| Mycobacterial species tested | rpo95/KY292 | KY290/KY292 |
|---|---|---|
| *M. marinum* | – | – |
| *M. flavescens* | – | – |
| *M. xenopi* | – | – |
| *M. simiae* | – | – |
| *M. brunense* | – | – |
| *M. chelonae* | + | + |

[1]A "+" entry indicates amplification, a "–" entry indicates no amplification.

EXAMPLE 6

PCR using MTB-specific Primers rpo105 and rpo273 in Combination with Less Specific Primers Degenerate primers DDIDH, NMQRQ(#2) and FENLFF (Table 2) were designed with reference to highly conserved amino acid sequences in the bacterial rpoB gene as described in Example 2 for DDIDHL and NMQRQ(#1) (FIG. 1). Like DDIDHL and NMQRQ(#1) they contained restriction sites to facilitate later cloning, if desired, as further described in the footnotes to Table 2. Primers rpo95, rpo105, rpo273, rpo293 and rpo397 were designed as described above in Example 2 and Example 4.

A. Bacterial DNA isolation. DNA from pure cultures of bacteria were prepared for polymerase chain reaction (PCR) amplification by one of the following methods:

Method BB/B. A 10-µL loopful of each isolate was placed in a 2.0-ml screw cap microcentrifuge tube (Sarsted, Inc.) that contained 1.0 ml of 1XTE (1X TE: 10 mM Tris (hydroxymethyl)aminomethane hydrochloride (Tris-HCl), pH 8.0, 1 mM ethylenediaminetetraacetic acid (EDTA), 100X concentrate purchased from Sigma Chemical Company, St. Louis, Mo.), 1% Triton-X100 (Sigma), and filled ⅔ full with 0.1 mm diameter zirconium beads (BioSpec Products, Bartlesville, Okla. 74005). Tubes were oscillated on a MiniBeadBeater mechanical disrupter Model 3110 (BioSpec Products, Bartlesville, Okla.) for 30 seconds. The supernatant was pipetted into a clean tube, boiled 30 minutes to kill the bacteria, and stored at –20° C. until needed. Two µL was used in a 50-µL PCR.

Method BB/P. A 10-1µL loopful of each isolate was placed in a 0.5 ml screw cap microcentrifuge tube that contained 0.3 ml of TE-equilibrated phenol (phenol from Boehringer Mannhelm Biochemicals, Inc., Indianapolis, Ind.), 150 µl 1×TE, and was filled ⅔ full with 0.1-mm diameter zirconium beads. The mixture was oscillated 30 seconds on a Mini Bead Beater. The tubes were allowed to sit at room temperature for 15–30 minutes to kill the bacteria, then centrifuged for 20 seconds in a microcentrifuge to separate phases. The aqueous phase was transferred to a new tube and stored at –20° C. until needed. Since these samples contained phenol (phenol is somewhat soluble in the aqueous phase), the DNA from these samples was extracted using either the IsoQuick nucleic acid extraction kit (MicroProbe, Garden Grove, Calif. 92641) or the Magic (now Wizard) DNA Cleanup kit (Promega Corp., Madison Wisc.). The resultant DNA extract from either procedure was suspended in 50 µl of water. Five µL of 1/10 or 1/100 dilutions of purified DNA in water was used as target for the PCR.

B. DNA extraction from clinical specimens. Clinical specimens (respiratory: sputum, induced sputum, bronchial wash/lavage; non-respiratory: gastric wash, urine, ankle tissue, groin tissue) were processed by 1% NaOH liquefaction-decontamination and sedimentation (Mayo Clinic Mycology and Mycobacteriology Clinical Laboratory Manual). The specimen that was leftover from standard clinical laboratory procedures was used for PCR analysis. the DNA was extracted from clinical specimens using one of the following methods:

Method L6/PBB. 200 µl of residual specimen was placed in a 1.5 or 2.0 ml screw cap tube and centrifuged for 10 minutes at 14,000×g. The supernatant was removed and the pellet suspended in 200 µl of L6 buffer (5M guanidinium thiocyanate), 1% Triton X-100, 50 mM Tris-HCl (pH 6.4), 20 mM EDTA) (Boom et al., *J. Clin. Microbiol.*, 1990). This material was transferred to a new 2 ml screw cap tube containing 750 µl phenol-chloroform-isoamyl alcohol (25:24:1) and ⅔ full of 0.1 mm zirconium beads. The tube was shaken in a MiniBeadBeater for 2 minutes. The tube was allowed to rest for 15 min to assure killing of unlysed organisms, then centrifuged for 2 min to separate phases and pellet debris. the top aqueous phase was transferred to a new 1.5 ml snap top tube and subjected to IsoQuick kit DNA extraction method with the following modification. At the point the DNA is to be precipitated, 1 µl of glycogen suspension (Boehringer Mannhelm Biochemicals, Indianapolis, Ind.) was added to promote the precipitation of DNA. This step was essential because of the wide variety of DNA concentrations present in these extracts. The resultant DNA pellet was suspended in 20 µl of water and stored at –20° C. until needed. Two µl of extracted material, or 2 µl of a 1/10 dilution of the extract in water, was used in the nested PCR procedure described below.

Method P/BB-2. 1.0 ml of residual specimen was placed in a 2.0 ml screw cap tube and centrifuged for 15 minutes at 14,000×g. The supernatant was removed, and the following were added to the tube: 600 µl TE equilibrated phenol, 400 µl 1X TE buffer, and 0.1 mm diameter zirconium beads (⅔ full). The tube was then oscillated for 30 seconds using the MiniBeadBeater, incubated at room temperature for 15 min to kill the unlysed organisms, and centrifuged for 3 min at 12,000×g to separate phases. The aqueous phase was transferred to a clean tube and stored at –20° C. until needed. The DNA from the aqueous phase was extracted using the IsoQuick kit. Five µM of a 1/10 or 1/100 dilution of extracted DNA in water was used for the PCR.

C. Polymerase chain reactions. Oligonucleotide primers DDIDH, NMQRQ(#2), FENLFF, rpo95, rpo105, rpo273, and rpo293 (Table 2) were synthesized using an Applied Biosystems Model 394 Synthesizer (Applied Biosystems, Foster City, Calif.) and standard phosporamidite chemistry (described in more detail in Example 5). The buffer and components (master mixes) used for PCR were as follows:

Master Mix I: This was the mix used for all non-nested PCRs and for the initial round of the hemi-nested PCRs described below. 5 µl target DNA was used per 50 µl PCR.

10 mM Tris-HCl, pH 8.3

50 mM KCl

10% glycerol 1.5 mM $MgCl_2$ 0.2 mM deoxyadenosine triphosphate (dATP)

0.2 mM deoxyguanidine triphosphate (dGTP)

0.2 mM deoxycytidine triphosphate (dCTP)

0.2 mM deoxyuridine triphosphate (dUTP) (all nucleoside triphosphates (dNTPs) from Boehringer Mannhelm Biochemicals, Indianapolis, Ind.)

0.125 μl/25 μl reaction AmpliTaq polymerase (5 units/μl, Perkin Elmer Cetus, Norwalk, Conn.).

1 μM of each primer

Master Mix II: 75 μl of this master mix was added to a 25 μl PCR containing the components of Master Mix I. The final concentrations were the molar amounts present in the 75 μl volume that was added:

10 mM Tris-HCl, pH 8.3

50 mM KCl

10% glycerol 1.5 mM $MgCl_2$ 0.25 mM of each dNTP (see Master Mix I)

2.5 units AmpliTaq polymerase 1.25 μM of each primer

Lysis and DNA extraction were done at one location, preparation of the PCR master mix at another, and amplification and amplicon analysis at a third to minimize the chance of contamination. In addition, the incorporation of dUTP facilitated elimination of any potentially contaminating amplified product. Either a Temptronic Series 669 (Barnstead-Thermolyne, Dubuque, Iowa 52004) or Perkin-Elmer Cetus Model 9600 thermal cycler was used.

Standard (non-nested) PCRs were carried out using the conditions described in Table 7. Hemi-nested PCRs make use of one upstream primer and two different downstream primers in two successive PCRs in order to provide greater sensitivity. Hemi-nested PCRs utilizing rpo105/rpo293 followed by rpo105/rpo273 were carried out in a single tube protocol. For the hemi-nested procedure an Ampliwax bead (Perkin Elmer Cetus, Norwalk, Conn.) was included in the first PCR reaction to act as a barrier to prevent inadvertant dilution and amplicon contamination of the work area. The first PCR employed rpo105/rpo293 as primers in a 25 μl reaction. Conditions for amplification are described in Table 7. Upon completion of this PCR, 75 μl of Master Mix II, containing primers rpo105/rpo273, was added to each tube (above the solidified Ampliwax layer). The tubes were then returned to the thermocycler. Conditions for the second round of amplification are also described in Table 7.

TABLE 7

| Primer Combinations | PCR Cycling Parameters* Temperature/Time |
|---|---|
| rpo95/rpo397 | 94° C./60 sec; 65° C./60 sec (50 cycles) alternative method 94° C./30 sec; 71° C./60 sec (50 cycles) |
| rpo95/rpo293 | 94° C./60 sec; 65° C./60 sec (50 cycles) |
| rpo95/NMQRQ | 94° C./30 sec; 61° C./60 sec; 72° C./60 sec (2 cycles) then 94° C./30 sec; 70° C./60 sec (50 cycles) |
| FENLFF/NMQRQ | 94° C./30 sec; 61° C./60 sec; 72° C./60 sec (2 cycles) then 94° C./30 sec; 65° C./60 sec (50 cycles) |
| DIDDH/NMQRQ | 94° C./30 sec; 61° C./60 sec; 72° C./60 sec (2 cycles) then 94° C./30 sec; 70° C./60 sec (50 cycles) |
| Single tube nested: | |
| rpo105/rpo293 | 94° C./30 sec; 72° C./60 sec (25 cycles) then |
| rpo105/rpo273 | 94° C./30 sec; 74° C./60 sec (50 cycles) |

Amplification products were detected by agarose gel electrophoresis of 1/5 or 1/10 of the reaction mixture in 2% agarose (Seakem GTG, FMC, Rockland, Me. 04841) made up in 1X Tris-borate-EDTA (TBE) (0.089M Tris-borate, 0.089M boric acid, 2mM EDTA), followed by staining with ethidium bromide. The products were purified by using Magic PCR Prep kit reagents (Promega, Madison, Wisc. 53711), and sequenced by using primer rpo95 at the Mayo Clinic Molecular Biology Core Facility using an Applied Biosystems 373A automated sequencer and the dye-coupled dideoxyribonucleotide cycle sequencing method (Applied Biosystems, Inc., Foster City, CA). Sequencing reactions were run using 5% (v/v) dimethylsulfoxide for twenty-five cycles of 96° C. (30 seconds), 50° C. (15 seconds), 60° C. (4 minutes). To provide additional detection sensitivity, Southern blots of agarose gels were prepared on nylon membranes (Nytran, #77593, Schleicher and Schuell, Keene N.H. 03431) by overnight capillary blotting followed by UV-crosslinking. The blots were probed with a 328-bp MTB rpoB amplification product of primers rpo95 and rpo397 which was directly coupled with horseradish peroxidase using ECL kit reagents according to the manufacturer's recommendations (Amersham, Arlington Heights, Ill. 60005). Hybridization conditions (42° C., 16 hours) specified by the kit manufacturer were used. Chemiluminescence was detected by exposure of Kodak AR X-ray film for 5 minutes.

Alternatively, a technique involving the use of single stranded comformational polymorphisms (SSCP) was used to visualize the amplification products derived from clinical specimens, as described in detail in Telenti, Antimicrobial Agents and Chemotherapy, 37, 2054–2058 (1993), which is incorporated herein by reference. PCR products from MDR-MTB exhibited the expected altered electrophoretic migration pattern from that observed for drug-sensitive MTB.

D. Results. The hemi-nested procedure described above incorporating oligonucleotide primers rpo105/rpo293/rpo273 was used to test a specificity panel consisting of drug-sensitive and -resistant M. tuberculosis, 15 species of mycobacteria other than M. tuberculosis (MOTT) and 7 additional G-C rich genera (Table 8). Successful amplification occurred only for M. tuberculosis and not with 23 non-MTB species (Table 8). In a blinded challenge panel consisting of 53 clinical specimens from a variety of anatomical sources this primer set was also successful in detecting rpoB in 19 multi-drug resistant MTB isolates, all of which were rifampicin resistant (Table 9).

TABLE 8

Specificity Challenge with Mycobacteria and Other G-C Rich Organisms Primer set rpo105/rpo293/rpo273 in a Hemi-nested PCR Mycobacteria M. asiaticum M. avium-intracellulare M. bordonii M. chelonae M. fortuitum M. gordonae M. kansasii M. malmoense M. marinum M. nonchromogenicum M. phlei M. scrofulaceum M. simiae M. smegmatis M. szulgai M. triviale M. tuberculosis
M. xenopi Other G-C Rich Genera Actinomyces sp.
Aerobic Actinomycetes
Corynebacterium sp.
Nocardia sp.
Probionibacterium sp.
Rhodococcus sp.

TABLE 9

Direct Detection of *M. tuberculosis* rpoB in 53 Clinical Specimen Panel

| | Results | | | |
|---|---|---|---|---|
| Specimen Source (n) | rpoB[1] | IS6110[2] | Smear[3] | Culture |
| Respiratory[4] (8) | + | + | + | MTB |
| Respiratory (11) | + | + | — | MTB |
| Respiratory (1) | + | — | — | MTB |
| Respiratory (2) | — | — | — | MTB |
| Respiratory (6) | — | — | — | — |
| Respiratory (3) | — | — | + | MOTT[5] |
| Respiratory (12) | — | — | — | MOTT |
| Respiratory (2) | — | +[6] | — | MOTT |
| Respiratory (1) | +[7] | — | — | MOTT |
| Respiratory (1) | +[7] | — | + | MOTT |
| Respiratory (1) | +[7] | — | — | — |

TABLE 9-continued

Direct Detection of *M. tuberculosis* rpoB in 53 Clinical Specimen Panel

| | Results | | | |
|---|---|---|---|---|
| Specimen Source (n) | rpoB[1] | IS6110[2] | Smear[3] | Culture |
| Non-respiratory[8-GW] (1) | + | + | — | MTB |
| Non-respiratory[8-U] (1) | — | — | — | MTB |
| Non-respiratory[8-A] (1) | — | — | + | — |
| Non-respiratory[8-G,GW] (2) | — | — | — | MOTT |

[1]Hemi-nested PCR using primer set rpo105/rpo293/rpo273.
[2]In vitro laboratory detection using IS6110.
[3]In vitro laboratory detection using acid fast smear.
[4]Includes sputum, induced sputum, bronchial wash/lavage.
[5]Mycobacteria other than *M. tuberculosis* (MOTT).
[6]False positive.
[7]Amplicon sequenced as TB; Repeat rpoB PCR was negative.
[8]GW: gastric wash; U: urine; A: ankle; G: groin.

All documents cited herein are incorporated by reference. The foregoing detailed descriptions and examples have been given for clarity of understanding only. No unnecessary limitations are to be understood therefrom. The invention is not limited to the exact details shown and described, for variations obvious to one skilled in the art will be included within the invention defined by the claims.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 970 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
CAGACGCTGT TGGAAAACTT GTTCTTCAAG GAGAAGCGCT ACGACCTGGC CCGCGTCGGT    60
CGCTATAAGG TCAACAAGAA GCTCGGGCTG CATGTCGGCG AGCCCATCAC GTCGTCGACG   120
CTGACCGAAG AAGACGTCGT GGCCACCATC GAATATCTGG TCCGCTTGCA CGAGGGTCAG   180
ACCACGATGA CCGTTCCGGG CGGCGTCGAG GTGCCGGTGG AAACCGACGA CATCGACCAC   240
TTCGGCAACC GCCGCCTGCG TACGGTCGGC GAGCTGATCC AAAACCAGAT CCGGGTCGGC   300
ATGTCGCGGA TGGAGCGGGT GGTCCGGGAG CGGATGACCA CCCAGGACGT GGAGGCGATC   360
ACACCGCAGA CGTTGATCAA CATCCGGCCG GTGGTCGCCG CGATCAAGGA GTTCTTCGGC   420
ACCAGCCAGC TGAGCCAATT CATGGACCAG AACAACCCGC TGTCGGGGTT GACCCACAAG   480
CGCCGACTGT CGGCGCTGGG GCCCGGCGGT CTGTCACGTG AGCGTGCCGG GCTGGAGGAG   540
CGCGACGTGC ACCCGTCGCA CTACGGCCGG ATGTGCCCGA TCGAAACCCC TGAGGGGCCC   600
AACATCGGTC TGATCGGCTC GCTGTCGGTG TACGCGCGGG TCAACCCGTT CGGGTTCATC   660
```

-continued

```
GAAACGCCGT ACCGCAAGGT GGTCGACGGC GTGGTTAGCG ACGAGATCGT GTACCTGACC     720

GCCGACGAGG AGGACCGCCA CGTGGTGGCA CAGGCCAATT CGCCGATCGA TGCGGACGGT     780

CGCTTCGTCG AGCCGCGCGT GCTGGTCCGC CGCAAGGCGG GCGAGGTGGA GTACGTGCCC     840

TCGTCTGAGG TGGACTACAT GGACGTCTCG CCCCGCCAGA TGGTGTCGGT GGCCACCGCG     900

ATGATTCCCT TCCTGGAGCA CGACGACGCC AACCGTGCCC TCATGGGGGC AAACATGCAG     960

CGCCAGGCGG                                                            970
```

( 2 ) INFORMATION FOR SEQ ID NO:2:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

```
TTGAATTCGA YGAYATHGAY CAYCT     25
```

( 2 ) INFORMATION FOR SEQ ID NO:3:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

```
GTCCCTGCAG GACGACATCG ACCAC     25
```

( 2 ) INFORMATION FOR SEQ ID NO:4:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

```
TTGGATCCYT GVCGYTGCAT RTT     23
```

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:5:

```
GGGATCCGCY TCCGYTGCAT GTT     23
```

( 2 ) INFORMATION FOR SEQ ID NO:6:

( i ) SEQUENCE CHARACTERISTICS:
( A ) LENGTH: 26 base pairs
( B ) TYPE: nucleic acid
( C ) STRANDEDNESS: single -continued ( D ) TOPOLOGY: linear ( i i ) MOLECULE TYPE: DNA ( x i ) SEQUENCE DESCRIPTION: SEQ ID NO:6:

CCCTGCAGTT CGAGAACCTG TTCTTC 26

( 2 ) INFORMATION FOR SEQ ID NO:7:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

CCACCCAGGA CGTGGAGGCG ATCACAC 27

( 2 ) INFORMATION FOR SEQ ID NO:8:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:8:

AGTGCGACGG GTGCACGTCG CGGACCT 27

( 2 ) INFORMATION FOR SEQ ID NO:9:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:9:

CGTTTCGATG AACCCGAACG GGTTGAC 27

( 2 ) INFORMATION FOR SEQ ID NO:10:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:10:

CGTGGAGGCG ATCACACCGC AGACGT 26

( 2 ) INFORMATION FOR SEQ ID NO:11:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:11:

-continued

GACCTCCAGC CCGGCACGCT CACGT 25

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:12:

GGCGATCACA CCGCAGACGT 20

( 2 ) INFORMATION FOR SEQ ID NO:13:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:13:

GGACCTCCAG CCCGGCA 17

( 2 ) INFORMATION FOR SEQ ID NO:14:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Asp Asp Ile Asp His Leu
1 5

( 2 ) INFORMATION FOR SEQ ID NO:15:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Asn Met Gln Arg Gln
1 5

Figure 3:
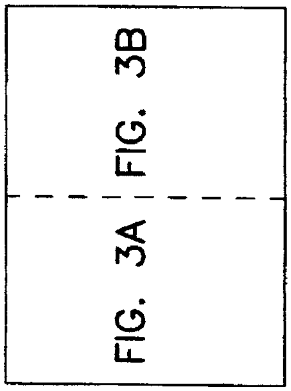
FIG. 3. A diagram and partial nucleotide sequence of the rpoB gene from M. tuberculosis (SEQ ID NO:1). Location of hybridization of oligonucleotide primers described in Table 2 is indicated by arrows and capitalized portions of the sequence. Boxed nucleotides indicate M. tuberculosis signature nucleotides described in Table 5.

What is claimed is:

1. A method for detecting Mycobacterium tuberculosis in a biological sample suspected of containing M. tuberculosis comprising:

(a) subjecting DNA from the biological sample to polymerase chain reaction using a plurality of primers under reaction conditions sufficient to simplify a portion of a M. tuberculosis rpoB gone to produce an amplification product, wherein the plurality of primers comprises at least one primer that hybridizes under hybridizing conditions to the amplified portion of the gone at a site comprising at least one position-specific M. tuberculosis signature nucleotide selected, with reference to FIG. 3 (SEQ D NO:1), from the group consisting a G at nucleotide position 2312,
a T at nucleotide position 2313,
an A at nucleotide position 2373,
a G at nucleotide position 2374,
an A at nucleotide position 2378,
a G at nucleotide position 2408,
a T at nucleotide position 2409,
an A at nucleotide position 2426,
a G at nucleotide position 2441,
an A at nucleotide position 2456, and
a T at nucleotide position 2465; and (b) detecting the presence or absence of an amplification product, wherein the presence of an amplification product is indicative of the presence of M. tuberculosis in the biological sample and wherein the absence of the amplification product is indicative of the absence of M. tuberculosis in the biological sample.

2. The method of claim 1 wherein the biological sample is a fluid or tissue sample from a human patient.

3. The method of claim 1 wherein the amplified portion of the gone comprises a DNA segment comprising at least one position-specific nucleotide associated with rifampin resistance.

4. The method of claim 3 wherein the DNA segment is represented by nucleotide positions 2370 through 2438 in FIG. 3 (SEQ ID NO:1).

5. The method of claim 3 further comprising analyzing the amplification product to determine the presence or absence of the at least one position-specific nucleotide associated with rifampin resistance.

6. The method of claim 5 wherein the presence of the at least one positions-specific nucleotide associated with rifampin resistance is indicative of a multi-drug resistant strain tuberculosis.

7. The method of claim 5 wherein the polymerase chain reaction comprises a hemi-nested polymerase chain reaction.

8. The method of claim 7 wherein the plurality of primers comprises at least three different primers.

9. The method of claim 5 wherein the primer comprises a 3' end nucleotide and wherein the M. tuberculosis rpoB gene comprises a nucleotide with which the 3' end nucleotide of the primer pairs during hybridization; and wherein the number of nucleotides of the M. tuberculosis rpoB gene separating the at least one position-specific signature nucleotide and the nucleotide with which the 3' end nucleotide of the primer pairs during hybridization is less than 4.

10. The method of claim 9 wherein the nucleotide comprising the at least one position-specific signature nucleotide is the nucleotide with which the 3' end nucleotide of the primer pairs during hybridization.

11. The method of claim 10 wherein the printer is selected from the group consisting of rpo105 (SEQ ID NO: 10), rpo273 (SEQ ID NO: 11), KY290 (SEQ ID NO: 12), and KY292 (SEQ ID NO: 13).

12. The method of claim 11 wherein the primer is rpo105 (SEQ ID NO: 10) or rpo273 (SEQ ID NO: 11).

13. The method of claim 2 wherein the plurality of primers further comprises at least one primer selected from the group consisting of rpo95 (SEQ ID NO: 7), rpo293 (SF, Q ID NO: 8), and rpo397 (SEQ ID NO: 9).

14. A primer having 14–50 nucleotides that hybridizes under hybridizing conditions to an M. tuberculosis rpoB gone at a site, all or a portion of which site is located within a region selected, with reference to FIG. 3 (SEQ ID NO: 1), from the group consisting of nucleotides 1945–1980, 2160–2190, and 2890–2910.

15. The primer of claim 14 which the primer comprises a 5' end having a nucleotide sequence encoding a restriction endonuclease cleavage site.

16. The primer of claim 15 wherein the primer is represented by a degenerate nucleotide sequence selected, with reference to Table 2, from the group consisting of FENLFF, DDIDH, DDIDHL, NMQRQ(#1), and NMQRQ(#2).

17. A primer having 14–50 nucleotides that hybridizes under hybridizing conditions to an M. tuberculosis rpoB gone at a site comprising at least one position-specific M. tuberculosis signature nucleotide selected, with reference to FIG. 3 (SEQ ID NO: 1), from the group consisting of:

a G at nucleotide position 2312, a T at nucleotide position 2313, an A at nucleotide position 2373, a G at nucleotide position 2374, an A at nucleotide position 2378, a G at nucleotide position 2408, a T at nucleotide position 2409, an A at nucleotide position 2426, a G at nucleotide position 2441, an A at nucleotide position 2456, and a T at nucleotide position 2465.

18. The primer of claim 17 further comprising a 3' end nucleotide, wherein the M. tuberculosis rpoB gene comprises a nucleotide with which the 3' end nucleotide of the primer pairs during hybridization; and wherein the number of nucleotides of the M. tuberculosis rpoB gene separating the at least one position-specific signature nucleotide and the nucleotide with which the 3' end nucleotide of the primer pairs during hybridization is less than 4.

19. The primer of claim 18 wherein the at least one position-specific signature nucleotide is the nucleotide with which the 3' end nucleotide of the primer pairs during hybridization.

20. The primer of claim 19 wherein the primer is selected from a group consisting of primer rpo105, primer rpo273, primer KY290, and primer KY292.

21. Primer rpo95 (SEQ ID NO: 7).

22. Primer rpo293 (SEQ ID NO: 8).

23. Primer rpo397 (SEO ID NO: 9).

* * * * *

UNITED STATES PATENT AND TRADEMARK OFFICE

CERTIFICATE OF CORRECTION

PATENT NO. : 5,643,723

DATED : July 1 1997

INVENTOR(S) : David H. Persing et al.

It is certified that error appears in the above-identified patent and that said Letters Patent is hereby corrected as shown below:

Title page, item [75] Inventors, please delete "John J. Hunt" and insert --John M. Hunt--; for the same inventor, please note he is from St. Paul, Minnesota.

Signed and Sealed this

Thirteenth Day of January, 1998

Attest:

BRUCE LEHMAN

*Attesting Officer* *Commissioner of Patents and Trademarks*

UNITED STATES PATENT AND TRADEMARK OFFICE

CERTIFICATE OF CORRECTION

PATENT NO. : 5,643,723
APPLICATION NO. : 08/250030
DATED : July 1, 1997
INVENTOR(S) : David H. Persing et al.

It is certified that error appears in the above-identified patent and that said Letters Patent is hereby corrected as shown below:

In the Claims

Column 25, line 62 (Claim 1), delete "simplify" and insert --amplify--; line 63, delete "gone" and insert --gene--; line 66, delete "gone" and insert --gene--.

Column 26, line 57 (Claim 1), delete "SEQ D NO: 1" and insert --SEQ ID NO: 1--; insert --of:-- after "consisting" at the end of line 57.

Column 27, line 10 (Claim 3), delete "gone" and insert --gene--; line 22 (Claim 6), delete "positions-specific" and insert --position-specific--; line 24 (Claim 6), insert --of M.-- before "tuberculosis"; line 42 (Claim 11), delete "printer" and insert --primer--.

Column 28, line 3 (Claim 14), delete "gone" and insert --gene--; line 7 (Claim 15), delete "which" and insert --wherein--; line 16 (Claim 17), delete "gone" and insert --gene--.

Signed and Sealed this
Thirtieth Day of July, 2013

Teresa Stanek Rea
*Acting Director of the United States Patent and Trademark Office*

Disclaimer

5,643,723 - David H. Persing; John J. Hunt, both Rochester, Minn.; Karen K. Y. Young, San Ramon, Calif.; Teresa A. Felmlee, Oronoco, Minn.; Glenn D. Roberts; A. Christian Whelan, both of Rochester, Minn. DETECTION OF A GENETIC LOCUS ENCODING RESISTANCE TO RIFAMPIN IN MYCOBACTERIAL CULTURES AND IN CLINICAL SPECIMENS. Patent dated July 1, 1997. Disclaimer filed January 8, 2016, by the assignees, Roche Molecular Systems, Inc., and Mayo Foundation for Medical Education and Research.

I hereby disclaim the following complete claim 21 in said patent.

*(Official Gazette, May 24, 2022)*

(12) INTER PARTES REVIEW CERTIFICATE (275th)

United States Patent (10) Number: US 5,643,723 K1

Persing et al. (45) Certificate Issued: Feb. 1, 2018

(54) DETECTION OF A GENETIC LOCUS ENCODING RESISTANCE TO RIFAMPIN IN MYCOBACTERIAL CULTURES AND IN CLINICAL SPECIMENS

(75) Inventors: David H. Persing; John M. Hunt; Karen K. Y. Young; Teresa A. Felmlee; Glenn D. Roberts; A. Christian Whelen

(73) Assignee: ROCHE MOLECULAR SYSTEMS, INC.

Trial Number:

IPR2015-00881 filed Mar. 13, 2015

Inter Partes Review Certificate for:

| | |
|---|---|
| Patent No.: | **5,643,723** |
| Issued: | **Jul. 1, 1997** |
| Appl. No.: | **08/250,030** |
| Filed: | **May 26, 1994** |

The results of IPR2015-00881 are reflected in this inter partes review certificate under 35 U.S.C. 318(b).

INTER PARTES REVIEW CERTIFICATE
U.S. Patent 5,643,723 K1
Trial No. IPR2015-00881
Certificate Issued Feb. 1, 2018

AS A RESULT OF THE INTER PARTES REVIEW PROCEEDING, IT HAS BEEN DETERMINED THAT:

Claim 21 is cancelled.

* * * * *